(12) United States Patent
Goetz

(10) Patent No.: US 10,535,427 B2
(45) Date of Patent: Jan. 14, 2020

(54) SYSTEM FOR PLANNING IMPLANTATION OF A CRANIALLY MOUNTED MEDICAL DEVICE

(71) Applicant: Medtronic, Inc., Minneapolis, MN (US)

(72) Inventor: Steven M. Goetz, North Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 8 days.

(21) Appl. No.: 15/866,718

(22) Filed: Jan. 10, 2018

(65) Prior Publication Data
US 2019/0214126 A1    Jul. 11, 2019

(51) Int. Cl.
| | |
|---|---|
| G06T 15/00 | (2011.01) |
| G16H 30/40 | (2018.01) |
| A61B 6/00 | (2006.01) |
| A61B 6/03 | (2006.01) |
| G06T 19/00 | (2011.01) |
| A61B 34/10 | (2016.01) |

(52) U.S. Cl.
CPC ............. *G16H 30/40* (2018.01); *A61B 6/032* (2013.01); *A61B 6/461* (2013.01); *A61B 6/487* (2013.01); *A61B 6/501* (2013.01); *A61B 6/5205* (2013.01); *A61B 6/563* (2013.01); *A61B 34/10* (2016.02); *G06T 19/00* (2013.01); *A61B 2034/102* (2016.02); *A61B 2034/105* (2016.02); *G06T 2210/41* (2013.01); *G06T 2215/16* (2013.01); *G06T 2219/004* (2013.01)

(58) Field of Classification Search
USPC ........................................................ 345/419
See application file for complete search history.

(56) References Cited

U.S. PATENT DOCUMENTS

| | | |
|---|---|---|
| 2005/0148852 A1 | 7/2005 | Tank |
| 2005/0245806 A1 | 11/2005 | Singhal et al. |
| 2006/0004422 A1* | 1/2006 | De Ridder ........... A61N 1/0529 607/45 |
| 2006/0094951 A1 | 5/2006 | Dean et al. |

(Continued)

OTHER PUBLICATIONS

Mulliken, et al., "Custom-Fit Radiolucent Cranial Implants for Neurophysiological Recording and Stimulation," J Neuroscience Methods, Feb. 2015; 15;241: pp. 146-154.

(Continued)

*Primary Examiner* — Weiming He
(74) *Attorney, Agent, or Firm* — Shumaker & Sieffert, P.A.

(57) ABSTRACT

Devices, systems, and methods pertain to planning and providing guidance for a cranial based implantation of an implantable medical device or devices. The collection of data, such as data pertaining to the skull of the patient, the scalp of the patient, the vascular structure or neurological structures in the head of the patient, is performed. The data may be in the form of images, such as images generated by X-ray, magnetic resonance imaging, CT-scan and fluoroscopy. A surgeon can use the collected data to determine, for example, whether the patient is a candidate for a cranial implantation, whether the patient's skull and scalp can support the implantation, what configuration of device should be implanted, where the device should be implanted, and how the surgical incisions should be made.

17 Claims, 15 Drawing Sheets

(56) References Cited

U.S. PATENT DOCUMENTS

| | | | |
|---|---|---|---|
| 2008/0123922 A1* | 5/2008 | Gielen | A61B 5/06 |
| | | | 382/131 |
| 2009/0281623 A1 | 11/2009 | Kast et al. | |
| 2009/0287271 A1* | 11/2009 | Blum | A61N 1/37247 |
| | | | 607/45 |
| 2012/0010711 A1 | 1/2012 | Antonyshyn et al. | |
| 2013/0123789 A1* | 5/2013 | Park | A61B 17/15 |
| | | | 606/88 |
| 2015/0217500 A1 | 8/2015 | Antonyshyn et al. | |
| 2015/0223832 A1* | 8/2015 | Swaney | A61B 17/3421 |
| | | | 606/130 |
| 2016/0206380 A1* | 7/2016 | Sparks | A61N 1/37247 |
| 2017/0000564 A1 | 1/2017 | Gordon et al. | |
| 2017/0265943 A1* | 9/2017 | Sela | G06F 19/00 |
| 2017/0265947 A1* | 9/2017 | Dyer | A61B 34/20 |

OTHER PUBLICATIONS

Brennan, "Production of Anatomical Models from CT Scan Data," De Montfort University, Leicester, United Kingdom, by Dublin Institute of Technology, School of Manufacturing and Design Engineering, Nov. 1, 2010, 146 pp.

Search Report and Written Opinion from counterpart European Application No. PCT/US2018/063556, dated Feb. 28, 2019, 10 pp.

\* cited by examiner

SYSTEM FOR PLANNING IMPLANTATION OF A CRANIALLY MOUNTED MEDICAL DEVICE

TECHNICAL FIELD

The disclosure relates to devices, systems, and techniques for planning and assisting with medical procedures and, more particularly medical procedures related to cranially mounted medical devices.

BACKGROUND

Implantable medical devices (IMDs) include devices implantable in a mammalian body that sense medical parameters, monitor medical conditions, administer therapy, or any combination thereof. Typical IMDs include a variety of electrical and/or mechanical components, often including a housing that houses the components. Because the components may be fragile, the housing is usually sufficiently robust to protect the components from forces to which they would otherwise be exposed when implanted within the body. Housings may be constructed from titanium, for example. In order to avoid potentially harmful interactions between the components and bodily fluids, such as corrosion, IMD housings are typically hermetically sealed.

Large components common to most IMDs typically include a battery, a coil, and a hybrid circuit that includes digital circuits, e.g., integrated circuit chips and/or a microprocessor, and analog circuit components. IMDs may include other components as well. The components and the housing each add bulk to the IMD.

Some medical devices may be implanted in the head of a patient. For example, an IMD may be implanted under the scalp and on top of the cranium, with one or more leads deployed on the head or implanted in the brain.

SUMMARY

In general, the disclosure is directed to techniques for planning and carrying out implantation of an IMD that is ultimately affixed to a portion of a skull of a patient. Implantation of a cranially implanted IMD may include making an incision in the scalp of the head of a patient to obtain access to the implantation site, and implanting the IMD at the implantation site. Implanting the IMD may include affixing the IMD, for example using some type of fasteners or an adhesive, to the skull of the patient, the IMD affixed to a portion of the exterior surface of the skull, or in some examples affixed either partially or wholly within a recess formed in the skull. Electrical leads, including one or more electrodes electrically coupled to circuitry within the IMD thru electrical conductors within the electrical lead(s), may extend from the IMD and through one or more openings in the skull to allow the one or more electrode(s) to be placed at a target structure, such as brain tissue, located within the skull of the patient having the implanted IMD.

The devices, systems, and techniques described in this disclosure may make implantation more efficient and improve the chances of success for the implantation. Generally speaking, data is collected prior to surgery that assists the surgeon in planning and executing the surgery. The collected data can pertain to various physical (e.g., anatomical and/or structural) parameters associated with the skull of the patient who is receiving the implanted IMD, such as data related to the contours of the skull of the patient, thickness of the skull in various portions of the skull, the condition of the scalp of the patient, the vascular structures and/or neurological structures in the head of the patient, prior electrophysiological measurements, and the like. The data may be in the form of images, such as images generated by X-ray, magnetic resonance imaging (MRI), computerized tomography (CT), EEG measurements, and fluoroscopy. The data can also be in the form of physical or virtual models of the patient's skull. Additional data related to the patient, for example the previous medical history of the patient, and other data, such as whether the patient wears glasses and/or hearing aid devices, and what activities the patient may participate in, such as exercise activities, may also be included in the collected data. In addition, data used by the devices, systems, and techniques described herein may include data associated with various IMD devices, and devices such as electrical leads including electrodes that may be incorporated into a system involving an IMD that is being considered for a cranially mounted implant procedure.

The systems, devices, and techniques described in this disclosure in some examples provide a graphical interface that allows a user, such as a surgeon who is evaluating and/or performing the implantation procedure for a particular patient, to graphically model various scenerios related to the proposed implantation based on the collected data, and in some examples based on inputs, such as threshold limits and other parameters that may be input to the system by the user, or for example via manufacturer's data associated with a device.

Using the graphical interfaces provided by the devices, systems, and techniques described in this disclosure, a user such as a surgeon may utilize the collected data to have generated and/or to manipulate graphical images based on the patient specific data to determine, for example, whether the patient is a candidate for a cranial implantation, and whether the patient's skull and scalp can support the implantation. The surgeon can also determine, using the generated graphical images, what devices may be best suited for an implant for the particular patient, where the device(s) may and/or may not be implanted, how to optimize post-implant performance of the device as it monitors brain signals and delivers therapy, and how the surgical incisions required to perform the implantation of the device(s) should be made, all factors to be considered to best optimize the implantation procedure and increase the likelihood of patient satisfaction with the implantation once completed.

In addition, the surgeon may use the graphical interfaces described in this disclosure to determine what configuration of device or devices, including what specific IMD or IMDs, should or could be implanted for a particular patient. Further, various levels of recessing of the IMD within the skull of a particular patient may be modeled using the devices, systems, and techniques described herein, to consider the procedural aspect of performing the implantation, and with respect to the physical and cosmetic aspects of a proposed implantation.

In one example, the disclosure is directed to a method comprising: receiving, at a processing circuitry, image data of a head of a patient; receiving, at the processing circuitry, an indication of one or more selected evaluation parameters; rendering, by the processing circuitry, a graphical image comprising a skull model based on the image data, the skull model comprising one or more image annotations superimposed onto the skull model, the image annotations determined based on an evaluation of the one or more selected evaluation parameters; and displaying, on a display device, the rendered graphical image comprising the skull model and the one or more image annotations.

In another example, the disclosure is directed to a system comprising: a processing circuit configured to: receive image data of a head of a patient; receive an indication of one or more selected evaluation parameters; and render a graphical image comprising a skull model based on the image data, the skull model comprising one or more image annotations superimposed onto the skull model, the image annotations determined based on an evaluation of the one or more selected evaluation parameters; and a display device configured to receive the rendered graphical image and to display the rendered graphical image comprising the skull model and the one or more image annotations superimposed onto the skull model.

In another example, the disclosure is directed to a non-transitory computer readable storage medium comprising instructions for causing processing circuitry to: receive an image data of a head of a patient; receive an indication of one or more selected evaluation parameters; render a graphical image comprising a skull model based on the image data, the skull model comprising one or more image annotations superimposed onto the skull model, the image annotations determined based on an evaluation of the one or more selected evaluation parameters; and output the rendered graphical image comprising the skull model and the one or more image annotations for display at a display device.

The details of one or more examples of the disclosure are set forth in the accompanying drawings and the description below. Other features, objects, and advantages of the disclosure will be apparent from the description and drawings, and from the claims.

DETAILED DESCRIPTION

Figure 1:
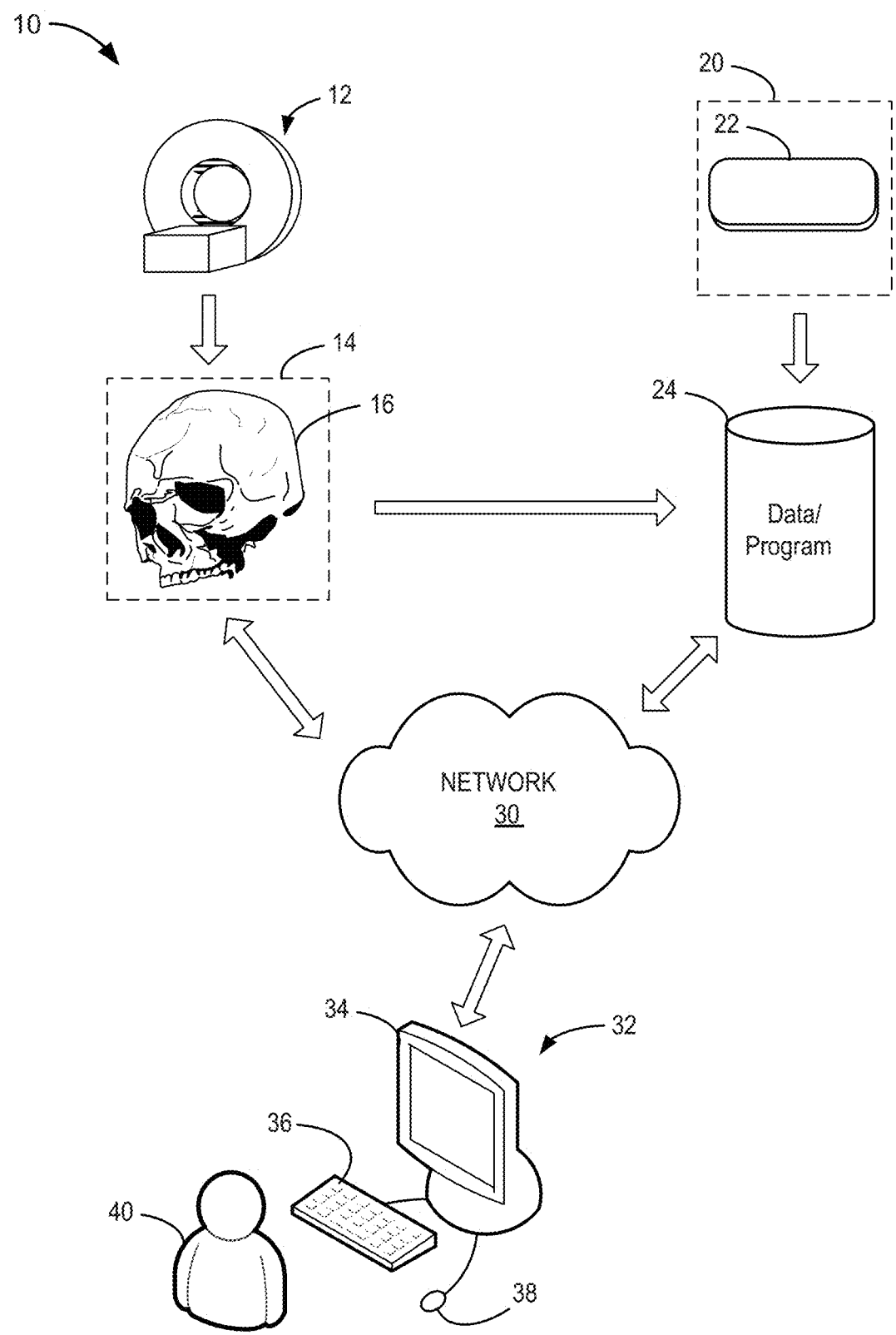
FIG. 1 is a conceptual diagram illustrating an example system in accordance with various techniques described in this disclosure.

A cranial based implantation of an IMD may include both the routing of one or more leads from an implanted IMD to a target structure, for example tissues of a patient, such as one or more portions of the brain tissue of the patient. The leads may include one or more electrodes positioned at the tip of the lead or leads, and/or along the lead body of the lead(s), the electrodes electrically coupled to electrical conductors included within the lead(s). The electrodes may be coupled through the electrical conductors to circuitry included within an IMD. The IMD may be arranged for providing stimulation, such as electrical stimulation therapy to the target structure, and/or for monitoring electrical signal, for example neurological signals associated with electrical activity of the brain that may be produced at or near the target structure. The IMD may function as a neurostimulator that provides deep brain stimulation (DBS) via leads and electrodes deployed in the brain of patient. In various examples, the IMD may be used to treat any nervous system disorder including, but not limited to, epilepsy, pain, psychological disorders including mood and anxiety disorders, movement disorders (MVD) such as, but not limited to, essential tremor and Parkinson's disease and neurodegenerative disorders.

As part of the cranial based implantation, the IMD itself may be physically mounted to an exterior portion of the skull of the patient, and the leads routed from a connection block of the IMD to the target structure. The IMD may be mounted so that an exterior surface of the IMD is placed in contact with an exterior surface of the skull of the patient. In some examples, the IMD is mounted so the that IMD is partially or wholly located in a recess formed in the skull of the patient. The implantation of the IMD may include making an incision in the scalp of the patient in the area where the IMD is to be affixed or otherwise located, and replacing the scalp over the implantation site and the IMD upon completion of the implantation procedure.

In some examples of a cranial based implantation, the routing of the leads from the IMD to the target structure includes routing the lead(s) under a portion of the scalp of the patient to one or more burr holes formed in the skull of the patient at a location that is different from the location on the skull where the IMD is located. The leads may be routed through the burr holes, and thus through the skull of the patient, to be positioned so that the electrodes of the lead(s) are positioned at or near the target structure. In other examples of cranial based implantation, the IMD is located at a position of the skull where the leads are to penetrate through the skull, and therefore the leads extend from the IMD directly through the burr hole(s) or a recess opening provided in the skull of the patient, and may be routed to the target structure without the need to route the leads between the scalp and the exterior portion of the skull between the location where the IMD is affixed and the position(s) of the skull where the electrodes extend through the skull to the target structure.

In some examples, the IMD itself may be positioned over and extend past the areas of the skull where the burr holes or the recess opening are formed. In other examples, a burr hole may be formed including a recess having a size and dimensions that allows the IMD to be implanted within the recess forming part of the burr hole, and having the leads extending directly from the IMD through the burr hole and to the target structure of the patient. In this case, the IMD may additionally play a role in securing the lead in place in the burr hole so that it remains fixated relative to the target structure.

For many cranial based implant procedures, portions of the procedure, including the implantation of the leads that may include the stimulation and/or recording electrodes, are planned preoperatively on a workstation designed for this purpose. This planning typically makes use of preoperative images (e.g., CT or MR) to localize a target structure, a trajectory through intervening tissue to get to the target structure, and an entry point on the skull consistent with the trajectory and selected according to a variety of additional criteria. This plan can then be mapped to stereotactic space using images of a localizer, or can be used intraoperatively with navigation tools to position the implant along the desired trajectory and at the desired target structure.

Such planning software may not include the capability to plan the other elements of the implantation procedure, in particular elements related to the IMD itself, such as positioning of anchors, placement of the extension or other connections to the implanted IMD, any tunneling that must occur, options for placement (cranially or otherwise) of the IMD, and/or the ability to model and determine various factors related to cosmetic aspects and other interference issues that may be of concern to the patient, for example interactions between the IMD and other devices such as glasses or hearing aids that may be worn by the patient. In addition, such planning software may not include the capability to plan an implantation procedure that include more than one IMD, for example a multi-device implant procedure, or an implant procedure involving the additional of an IMD to a patient having an existing IMD implant. Such planning software may not provide assistance in placing a device so as to optimize its ability to record brain signals post operatively. These factors and considerations may be important, and such details associated with the cranial based implantations may impact the system's performance and the patient's acceptance of the therapy (due to comfort, cosmetic, or other issues). Various examples of the modeling system and techniques described in this disclosure allow for extending the planning process associated with a cranial based implantation to include tools that may allow a both a surgeon and a patient to evaluate many additional factors associated with a proposed implantation procedure.

Moreover, advances in active medical devices now allow miniaturization of IMDs such that the smaller devices may be implanted in new anatomical locations not previously possible or practical for IMD placements. One such location of particular interest is implantation on the cranium, such that the surgical procedure related to therapies such as deep brain stimulation is mimimized. By implanting the IMD device itself on the cranium, surgical steps are reduced (fewer incisions, less tunneling), hardware is reduced (eliminate extension and connections needed to reach the pectoral space), and the comfort and appearance of the patient may be optimized.

However, the optimum location for such a cranially mounted system may vary from patient to patient, and may not easily be determined by the implanting clinician. Patient head size and shape may vary considerably, such that the best location is not consistent. Skull thickness may also vary, both between patients and across different skull locations within a patient. Individual patient needs may vary, such as the relative importance of cosmetic impact given the presence (or absence) of hair. The location of signals of interest to be recorded from the patient's brain structures or cortex may vary as well. Surgical complication risk factors may vary, for example based on such factors as the thickness or robustness of the scalp of the patient. Procedural factors may also be relevant, such as the type of surgical frame used during the implant procedure and its manner of fixation to the skull, which may afford or deny potential implant locations.

In view of these many considerations and factors, implantation procedures and planning of cranially mounted IMDs may be highly disruptive due to both patient and physician acceptance. For example, identifying the ideal or optimal implant location for a cranially mounted device often requires balancing multiple factors, including but not limited to the anatomy of the patient receiving the implant (e.g., skull size, shape, thickness, scalp thickness), patient desires (e.g., cosmetic implications, interference with glasses or other activities), and surgical concerns (e.g., minimization of erosion of skin at or near the implantation site, infection, compatibility with other surgical tools like frames and fixturing used for performing the implantation). Since the target and trajectory of a lead intended for deep brain stimulation may already be planned using preoperative images and specialized workstation, the devices, systems, and techniques described in this disclosure provide tools to extend that planning procedure to include planning the location on the cranium on the skull of the implantable device, and/or planning for the implantation procedure itself.

Use of the devices, systems, and techniques described in this disclosure, such as the user workstation illustrated and described with respect to FIG. 1 below, may provide patient specific guidance, based for example on preoperative images and preferences specific to the patient, useful in determining a satisfactory or preferred location for implantation of an IMD, for providing inputs on tool selection and workflow associated with the implantation procedure, and may potentially aid the surgeon via navigation during the actual implantation procedure. Use of the examples of devices, systems, and techniques described in this disclosure may help guarantee a high degree of patient satisfaction with respect to factors such as cosmetic concerns addressed before surgery, predictable recharge and telemetry performance, optimized brain signal recording conditions, and an efficient surgical procedure (e.g., planned location, lead management, tool/template selection complete before first incision), and reduce the risk of surprises in the operating room (e.g., lead too short, bone too thin) or postoperative complications (e.g., high profile implantation that leads to infection).

Optimizing the implant location preoperatively may help ensure patient satisfaction, may drive an efficient surgical procedure, and may minimize intraoperative or postoperative complications. Extending the capabilities of an existing MDT stereotactic planning station to include the ability to plan the placement of a cranially mounted medical device may provide additional guidance to the surgeon based on patient specific anatomy (size, shape, thickness of skull and scalp), preferences of the patient (e.g., cosmetic concerns), surgeon considerations (e.g., desired procedure, tool compatibility), best practices (e.g., minimizing infection/erosion), and technical considerations (e.g., min/max separation to enable recharge or telemetry, signal recording considerations).

Although the devices, systems, and techniques described in this disclosure refer to the modeling, planning, and/or procedures associated with a cranial based implantation, these devices, systems, and techniques are not limited for use in cranial based implantation procedures, and may be utilized in medical procedures related to the implantation of IMDs in other areas of a patient, such as spinal or pelvic areas of a patient.

FIG. 1 is a conceptual diagram illustrating an example system 10 in accordance with the various techniques described in this disclosure. As shown in FIG. 1, system 10 includes imaging equipment 12 coupled to a user workstation 32 through a network 30. Workstation 32 may be arranged to store data and/or programming associated with the modeling and planning techniques described in the disclosure, and any equivalents thereof. Workstation 32 may include processing circuitry (not specifically shown in FIG. 1), including one or more processors that are configured to execute instructions causing workstation 32 to perform one or more of functions and to provide various features described throughout this disclosure, and any equivalents thereof, related to the modeling, planning, and/or guidance techniques that may be provided by system 10.

System 10 may include one or more pieces of imaging equipment 12 arranged to take images and to gather patient data 14 related to a skull and/or a scalp of a patient. Imaging equipment 12 is not limited to any particular type of imaging equipment, and may include device(s) arranged to generate images using X-ray, MRI, CT, and/or fluoroscopy. The collected patient data 14 generated by the imaging equipment 12 may pertain to the skull size and contours of the skull of the patient, thickness of the skull in various areas, the condition of the scalp of the patient including scalp thick and/or location and condition of the hair at various locations of the scalp, and the vascular structures and/or neurological structures in the head of the patient.

In some examples, patient data 14 captured by imaging equipment 12 may be processed by the imaging equipment and/or stored in a database 24. Patient data 14 may also include electrophysiological information, such as EEG data associated with the patient. This data may be incorporated into the modeling of a proposed implantation, for example to help optimize the location of recording electrodes of the device to be implanted that may be utilized to sense these electrophysiological signals. The data stored in database 24 as provided by imaging equipment 12 is not limited to any particular type of data, and may be any data generated through the operation of the imaging equipment 12 associated with a patient. In various examples, additional data may be generated based on further processing of the images and/or data generated by the imaging equipment 12, wherein the additional generated data may include data related to the skull size and dimensions of a skull of a patient, data related to the thickness profile of the skull of the patient, and/or data related to the scalp of the patient, including data related to blood vessels and/or nerve locations in the scalp of the patient. Data stored in database 24 may be associated with a specific patient, for example with a name of the patient, or with a patient ID number assigned to the patient. In some cases, database 24 may store population data obtained from multiple other patients, such as those that had previously undergone implant procedures. Workstation 32 may be coupled to database 24, either directly or for example through a network such as network 30. Workstation 32 may be configured to retrieve data stored in database 24, and to store data into the database 24. Network 30 is not limited to any particular type of network, and may include a Local Area Network (LAN), a Wide Area Network (WAN), a Storage Area Network (SAN), a Virtual Private Network (VPN), and may incorporate the Internet. Network 30 is not limited to communication provided in a particular format or using a particular protocol, may provide communicative links using for example Internet Protocol (IP) and/or using wireless network protocols such as Wi-Fi or Bluetooth.

In some examples, the patient data 14 provided by imaging equipment 12 and additional data emerged from the data provided by the imaging equipment (also referred to as patient data 14), may be used to generate one or more versions of a patient skull model 16. The skull model 16 may in some examples be generated, at least in part, by the imaging equipment 12. In other examples, the skull model 16 may be generated by processing circuitry included within workstation 32, and then stored back into database 24, or stored within the workstation.

As described above, system 10 includes a user workstation 32, which in some examples includes processing circuitry (not specifically shown in FIG. 1), including one or more processors that are configured to execute instructions to perform one or more of the functions and to provide various features described throughout this disclosure, and any equivalents thereof, related to the modeling, planning, and or guidance techniques that may be provided by system 10. For example, workstation 32 may be configured to retrieve data stored in database 24 and/or data stored within the workstation, and to render graphical images of a patient's skull, with or without image annotations as further described below, for display at the workstation. Workstation 32 may also include one or more input devices (such as keyboard 36 and/or a computer mouse 38), that are coupled to an Input/Output (I/O) port of the workstation (not specifically shown in FIG. 1), that allow a user, such as user 40, to provide inputs to the workstation. The user provided inputs may include inputs that allow manipulation of the graphical images being displayed at the workstation. The user provided inputs may also include inputs of data, such as data related to a patient, or data related to threshold values that may be used to control and otherwise manipulate the graphical images and/or the image annotations being displayed at the workstation.

Workstation 32 as illustrated in FIG. 1 includes a display device 34, that may be configured to provide a visual output of information, including graphical illustrations of a patient skull model, along with various other aspects associated with the skull model, as described throughout this disclosure. Display device 34 is not limited to any particular type of device, and may comprise a cathode ray tube (CRT), a liquid crystal display (LCD), a light-emitting diode (LED) display, a plasma display, or an organic Light emitting diode (OLED) display. In various examples, display device 34 comprises multiple screens, wherein the screens are configured to allow an image rendered and displayed on one screen to be moved to another screen, for example using a dragand-drop function, so that a first graphical image, such as a first skull model, may be superimposed over another graphical image, such as a second skull model. In various examples, display device 34 may be further configured to operate as a touchscreen device that allows a user, such as user 40, to provide inputs to user workstation 32 via inputs to display device 34, for example by touching the display surface of display device 34 using a wand or the user's finger. Other input devices, such as a computer tablet and stylus, may be included as part of user workstation 32 that would allow a user, such as user 40, to provide inputs to workstation 32, as would be understood by one of ordinary skill in the art. In various examples, the modeling, planning, and/or guidance techniques provided through workstation 32 may include allowing a user, such as a physician, to visualize a surgical procedure for a patient using a virtual reality environment generated by application(s) running on workstation 32, and displayed for example by display device 34. In various examples, the modeling, planning, and/or guidance techniques may include devices arranged to provide an augmented reality representing a surgical plan which may be visually provided, for example using display device 34, but in association with the patient's actual head as opposed to a rendered image of the patient's head.

Workstation 32 may be configured to access patient data 14, such as data associated with a patient skull model 16, for rendering as a graphical image for display on display device 34. In some examples, the visual display includes a rendering and display of graphical images of portions of a skull and/or scalp of a patient based on data that is being generated in real time by one or more of the imaging equipment 12. In some examples, workstation 32 is configured to receive inputs from a user, such as user 40, and to use the received inputs to control the imaging equipment 12 in real time during one or more processes being performed to capture patient data by the imaging equipment. For example, the movement, positioning, and image capturing operations of the imaging equipment 12 may be controlled by inputs received at the user workstation 32, and communicated to the imaging equipment 12 through network 30. In this manner, a user 40 may control the imaging equipment 12 to capture and/or store patient data 14, such as image information relate to the skull, scalp, and/or hair of the patient that may be used by system 10 to develop the one or more patient models and/or patient data that system 10 may then use for the modeling and planning procedures described throughout this disclosure. In addition to modeling of the skull and/or scalp of the patient, another consideration that may be taken into account in some manner by the modeling is the presence of one or more previously implanted cranial devices. For example, a planned surgical procedure may consider the implantation of a second-generation system or device to replace a first-generation system/device. In such examples, the location of the first implanted system or device may be important. For example, when considering the second implantation procedure, one might want to avoid the areas where bone had previously been removed as part of the first implantation procedure, or with regards to other factors, such as areas of the skull were fasteners were used to secure the first implanted device. Also, other cranial systems, such as cochlear implants, might also be shown during the planning process.

In various examples, system 10 further includes device data 20 related to one or more implantable medical devices 22 that may be implantable or otherwise affixed at some location on a skull of a patient. Medical devices 22 are not limited to any particular type or configuration of medical devices, and may include any of the IMDs as described throughout this disclosure or otherwise existing devices or devices developed at some future date that may be affixed to the skull of a patient. Device data 20 may include various types of data associated with the physical aspects of the medical devices 22, such as physical dimensions associated with the devices, including dimensions that define or otherwise quantify contours of the outside surfaces of the devices. Additional data associated with the medical devices 22, such as the weight of the devices, center of gravity information for the devices, and mounting, implantation, and/or fixation techniques that may be in configured for use with the different devices included as medical devices 22 may be included in device data 20. Other information, such as temperature or ranges of temperatures generated by the medical device 22 when operating the device, battery life, and/or parameters associated with recharging a rechargeable power source located within the medical devices 22 may also be included as part of device data 20. Additional factors that may be considered for a particular medical device 22 may include brain signal recording capabilities of the device. For example, the placement of recording electrodes, in some examples using the case of the device as one of these recording electrodes, and how these electrodes may be placed and oriented as part of the implantation procedure, may be considered and modeled in order to optimize the recording capabilities of the device once the device has been implanted. In various examples, device data 20 may be stored in database 24 and/or within workstation 32 for use by system 10 in modeling, planning, and providing guidance for the implantation procedure that may be performed on a patient using one or more selected medical devices 22.

In various examples, workstation 32 is configured to process data 14 related to a patient, as generated by imaging equipment 12 and/or as stored in database 24 and/or within workstation 32, and to generate images, such as patient skull model 16. By providing additional inputs to user workstation 32, the skull model 16 may be configured to be illustrated on display 34 with various types of data, and/or to provide other forms of information, either in the form of tabular data or in the form of a graphical depictions, for example image annotations, related to the skull model. For example, a depiction of skull model 16 rendered and displayed as a three-dimensional graphical image on display 34 may include one or more image annotations that are indicative of skull thicknesses at various locations of the skull model. The skull model 16 provided as a three-dimensional graphical image on display device 34 may include dimensional information for one or more dimensions, shapes, or sizes associated with the skull model.

In some examples, the skull model 16 may be provided as three-dimensional graphical image including image annotations illustrating information related to the scalp thickness of a patient at various positions relative to the skull of the patient. The skull model 16 provided as a three-dimensional graphical image on display device 34 may include information depicting a minimum amount of space the must be provided around an IMD graphically illustrated as being implanted on the skull model with respect to another medical device for assuring proper operations such as recharging, telemetry, signal quality and/or operating temperatures associated with the illustrated implanted IMD. The skull model 16 may be provided as a three-dimensional graphical image on display device 34 including image annotations illustrating information related to the location of blood vessels and/or nerve fibers located in the scalp of the patient.

The information, including image annotations, that is displayed in conjunction with a skull model is not limited to any particular type of information or to any particular format of information. In some examples, information such as skull thicknesses may be indicated by a several numbers superimposed over the skull model at different locations over the surface of the skull depicted in graphical image of the skull model, the numbers indicative of a skull thickness in that area of the skull of the patient. In some examples, different colors may be provided as colorings for different areas or regions of the exterior portions of the graphical image of the skull model being displayed to indicate one or more parameters associated with the skull. For example, a first color may be superimposed over portions of a displayed skull model to indicate a thickness, such as a minimum thickness, or a thickness that falls within a range of thicknesses, for that portion of the skull. One or more different colors may be superimposed over portions of the model of the patient skull to indicate a different thickness, or a different range of thicknessess, for the skull in the area where the different color is provided.

These types of indications are not limited to being provided in the graphical image with respect to any particular parameter associated with the skull being depicted by the skull model, and may be configured to represent data associated with skull thickness, skull shape (e.g., skull contours or flatness), skull size, scalp thickness and/or scalp condition, presence of absence of hair in various locations, locations where cortical or other brain signals are more easily recorded, and indications related to the blood vessels and/or nerves that may be present in different portions of the scalp, and/or minimum or maximum spacings that need to be maintained between devices when more than one device may be implanted on a skull of the patient being modeled.

Workstation 32 may also be configured to retrieve data, such as data 20 related to one or more medical devices 22, that may be under consideration for use as an implanted IMD for a patient. The data 20 related for example to an IMD may be rendered and used to generate a graphical image of the IMD based on data 20, and may be superimposed onto a three-dimensional graphical image of the skull of a patient. The particular device to be rendered and superimposed on the graphical image of the skull may be selected, for example by inputs to workstation 32 by user 40, from a plurality of devices for which device data 20 is available, and may be a device that a user 40 wants to model for display at workstation 32 for the purpose of evaluating the use of the selected device for implantation on the skull of the patient associated with the three-dimensional skull image.

For example, a three-dimensional image of a selected device 22 may be rendered by the processing circuitry of workstation 32 to provide an image of the device 22 that is then superimposed onto a three-dimensional image of the skull of a patient. Inputs received at the workstation 34 provided by user 40 may be used to control the rendering of the image for example with respect to the placement and/or orientation of the selected device 22, and for example with respect to various parameter associated with the implantation of the selected device 22. For example, user inputs to workstation 32 may be used to determine whether the user 40 wants to see the selected device 22 rendered and superimposed on the graphical image of the skull including the use of a recess formed in the skull at the graphically illustrated implantation site, versus seeing the graphical image of the selected device attached to the three-dimensional image of the skull without the use of a recess.

As part of the rendering of the graphical image having the selected device 22 displayed as superimposed on the graphical image of the skull, the workstation 32 may also be configured to provide additional information, for example in the form of one or more image annotations, as part of the display provided at the workstation. For example, workstation 32 may be configured to display an indication of the areas of the skull as part of the proposed implantation that would provide a skull thickness that would be adequate to allow implantation of the selected device. In the alternative, or in addition to these indications, the graphical image of the skull may provide image annotation that indicate areas of the skull where the skull thickness, or for example the contour of the skull in that area, would prevent or would not necessarily be optimal or recommended for use as the implantation site when considering implantation of a particular selected device 22.

In various examples, based on the proposed use of selected device 22, and a proposed implantation location, workstation 32 may be configured to generate a graphical image showing how the selected device may appear following the implantation based on various data, such as patient data 14, related to the thickness and overall condition of the scalp of the patient in the area of the proposed implantation. In addition, various additional image annotations may be provided as graphical outputs on display device 34 once a proposed implantation site for a selected device 22 has been provided as inputs to the workstation 32. For example, workstation 32 may be configured to generate a graphical indication of a boundary, or to provide some other form of a graphical indication displayed on display device 34, indicative of an area that surrounds the proposed implantation site and that indicates the area of the skull where a second device may not be implanted based on various consideration associated with the selected device 22.

The various considerations associated with the selected device may include factors such as minimum separation distance or maximum separation distances due to recharging, telemetry, sensing signal quality, or other considerations associated with the operation of the selected device in proximity to another device, such as another IMD. In other examples, the area indicated by the boundary or some other form of a visual indication, such as color, may indicate the maximum distance away that a second device may be located from the proposed implantation site for the proposed implantation site of the selected device 22 based on any requirements related to the operations of both devices together, for example having the capability to recharge both devices using a same recharging device, system, or recharge process.

In addition, once a proposed implantation site for the selected device 22 has been provided as inputs to workstation 32, the workstation may be configured to provide additional information, including the display of three-dimensional information and/or tabular information, related to other aspects of the proposed implantation, such as required lead lengths, proposed lead routes, and the impact of the proposed lead routings on blood vessels and/or nerves in the scalp of the patient. For example, one of the considerations for blood vessels may be regarding the incision used as part of the implant procedure. Surgeons implanting a medical device may try to cut parallel to the path of blood vessels in the areas of the implantation rather than across them, so that as few blood vessels as possible are cut due to the incision. As part of modeling an implantation procedure, the system may visualize direction of dominant vessel flow (for example based on a contrast enhanced imaging—where contrast agents are injected to help vessels show up on imaging) and then provide feedback/suggestions as to which direction to make the incision to minimize disruption to the blood vessels during and as a result of the implantation procedure.

In some cases, a database of patient population data may be provided that may include information about prior cranial implant procedures performed for other patients. Such information may include physical characteristics of prior patients, including skull shape and size, scalp thickness, hair characteristics, etc. Data may also include type and model of implantable device(s), lead(s) and any lead adaptors or extensions used to provide therapy, the type of therapy delivered, any complicating circumstances, whether the prior patients had other implantable devices, whether the patients used objects such as glasses or hearing aids that required consideration, some indication of physical appearance post-surgery, and so on. Population data may be compared to data associated with a current patient to suggest what aspects of a procedure may work well for the current patient and what aspects might be best avoided. This may help a clinician more quickly arrive at a best-fit model for the current procedure. In some cases, the system may use this data to suggest a starting point for a model that can then be modified by the clinician.

The ability of system 10 and workstation 32 to generate graphical images as described above with respect to FIG. 1 and as described throughout this disclosure allows a user, such as a surgeon, to place an image of a selected medical device 22, such as an IMD, on the skull model of a specific patient, such as skull model 16, and to test various locations as possible implantation sites for the IMD to evaluate the possible implantation sites, including through the graphical images displayed at display device 34. The information provided as the graphical images presented at display device 34 and the ability to manipulate these images to provide additional information may help a surgeon, and also a patient, to visualize the potential fit of different IMDs, to discover any potential drawbacks or obstacles related to the chosen implantation site for one or more IMDs, to consider options related to use of a recess in the skull as part of the implantation, to help understand the additional requirements related for example to lead placement and lead routing, and to consider various aspects involving multi-device implantations, and/or to better understand the related issues such as patient concerns including cosmetic and interference issues that may be of importance to the patient.

The graphical images and the additional information including image annotations that may be generated by system 10 may guide placement of an IMD by showing a surgeon potential "good" regions for the implantation of the IMD based on factors that are specific to the patient receiving the implant, such as size and shape (e.g., curvature/flatness) of the skull of the patient, thickness of the skull of the patient in different portions of the skull, thickness of skin in the scalp areas of the patient that may be affected by the implantation, or signal locations within this patient's brain. System 10 allows single factors, such as the skull thickness, shape, size, or factors associated with the scalp of the patient to be viewed individually, or to be combined as an overall 'goodness' metric, potentially weighted by patient and surgeon inputs (e.g., input parameters related to 'minimize complication risk, but weighting cosmesis as being of less concern'). The factors may be indicated in the graphical images rendered and displayed at workstation 32 by one or more image annotations, using for example different colors, shading, and/or using boundary lines, showing regions on a skull model that include modified color or other overlays on an existing skull image, and that may be modified by providing inputs that change or modify the parameters associated with these parameters as used to generate the images being provided at the workstation 32. The graphical images rendered and display at workstation 32 including one or more image annotations may include use of numbers, letters, and/or other graphical symbols superimposed on the graphical image of the skull model to indicate a ranking or some other value or values for one or more metrics associated with the skull, the scalp, or for example a patient preference associated with a proposed implantation procedure.

As part of the image annotations provided as part of display of the graphical image of a skull model of a patient, regions to avoid might also be shown based on selection of a specific procedure type. As an example, during surgery, a stereotactic head frame may be attached to the patient's skull to aid in implantation. To accommodate this, frame attachment regions of the skull might be indicated in a graphical image of a skull model provided at display device 34 that are indicative of areas to avoid so as not to interfere with surgical access during placement of a device, or for example that may be inaccessible due to the attachment of a particular frame or fixture used as a tool during the implantation process.

In another example, once a region of the skull for implantation of an IMD is selected, the system 10 may be configured to display a predictive model of the resulting cosmetic effect by stretching simulated skin over the implant location. This rendering of the model of the skull with a simulation of the skin at the implantation location may be based on patient specific measures of skin thickness obtained from the patient data, such as patient data 14 provided through the use of imaging equipment 12. If the cosmetic result of the optimal location is not acceptable, system 10 may guide the surgeon in selecting a region of skull in which to countersink the device. This might be influenced by patient specific factors extracted from images (thickness, curvature of skull), preferences selected by the surgeon or patient (e.g., to avoid behind the ear due to glasses, hearing aids), or known clinical consequences of certain locations (e.g., higher/lower risk of infection or erosion, unacceptable weakening of skull).

In some cases, guidance for a current patient may be based, at least in part, on patient population data, such as population data based on patients that previously underwent similar procedures and/or have similar patient-specific factors as those factors that are associated with the current patient (e.g., wears glasses, employs hearing aids, has thinning hair, has a similar skull curvature, etc.). The patient population data used for this guidance may further be limited to that associated with past procedures that were thought to represent favorable outcomes. In alternative scenarios, the patient population data may be associated with similar patient scenarios but represent unfavorable outcomes and thereby provide guidance on locations to avoid. A user-specified filter may be used to select the patient population data employed for providing guidance for the particular patient.

In any the foregoing examples, the guidance may be presented as a color overlay (as above) of the three-dimensional image of the skull of the patient indicating regions of the skull where a desired countersink depth could/could not be performed, or simply as raw data such as thickness of skull provided for example as numbers superimposed over the exterior surface of the image to the skull. Such guidance may include an indication of one or more of the allowable sink depth, desired sink depth, remaining bone at a given sink depth, remaining profile at a given sink depth, regions where a desired profile could/could not be achieved at the various regions of the skull. Once a selected countersink depth for a recess where the IMD may be implanted has been made, the predicted model of cosmesis given simulated skin stretching could again be rendered and presented as a graphical output at display 34 of the workstation. This image might be compared against a graphical image of non-countersunk implantation at the same proposed location on the skull, for example interactively observed as the variations of the depth/location/orientation of the countersink is varied by the user.

In some examples, given a final selected plan for a particular IMD to be implanted at a chosen implantation site and using a selected orientation, recess/non-recessed implantation, workstation 32 may be configured to produce metrics, that may include metrics related to final profile (max, average, min) dimensions associated with the IMD device extending above the skull with and without skin, amount of bone removed (max, average), amount of bone remaining (min, average), estimated time impact to the surgery, and length of lead needed from planned burr hole to planned cranial mount of the selected IMD. In some examples, if these parameters and/or generated metrics fall outside of clinical best practices, the user might receive a warning indication, (e.g., 'warning: planned countersink leaves less than 2 mm bone remaining'), as for example a visual output displayed on display 34 of workstation 32.

System 10 may also be configured to allow the routing of the lead(s) to be coupled to the IMD as part of the implantation to be planned using drag and drop or other interactive tools, given all of the information above. This may include indications of allowable lead length (e.g., 'warning: 28 cm lead length exceeded with desired location'). Warnings, for example in the form of an output provided on display 34, may be given if the plan does not meet known best practices (e.g., 'warning: insufficient strain relief loop').

In procedures where multiple devices are to be used, and where the constraints on positioning of the devices relates to minimum separation distances, or in other examples, to maximum separation distances, due to recharge, telemetry, sensing signal quality, or other considerations, system 10 may be configured to provide guidance on location of the second device given a first planned implantation location. Such guidance may be provided in the form of a visual indication, such as one or more colored regions and/or a boundary line that encircles or partially surrounds an area of the image of the skull of the patient based on a proposed implantation site for one or both of the devices to be implanted. Such guidance related to multiple devices may also allow the user to view consequences of the implant, such as the location/size/shape of a predicted magnetic resonance (MR) artifact created by the device. The guidance related to multiple devices may also preview the recharging configuration needed by the patient and predict recharge performance based on parameters of the selected location (depth of countersink, ability to get parallel coupling given curvature) and the patient's anatomy (skin thickness).

System 10 may also be configured to provide guidance related to specific tools to be used to position the selected medical device during the implantation procedure, and/or tools used to create the countersink recess in the skull where the IMD is to be placed. For example, system 10 may be configured to provide informational messages, displayed for example as text provided by display device 34, that include messages related to which tools may be used for a particular proposed implantation being illustrated by the display device. An example message might include text stating, "Use the green 2 mm countersink template" when referring to a proposed implantation including use of a recess formed in the graphical image of the skull of the patient. System 10 may also provide instructions for how to configure a tool or tools, for example a settable depth stop for countersink control. System 10 may be configured to generate data that would allow a device, such as a 3-D printer (now shown in FIG. 1) to produce a patient specific fixture via 3D printing or other techniques.

In a navigated procedure, where system 10 is configured to provide guidance to a person such as a surgeon performing the actual implantation process, system 10 may be configured to direct the user to the selected implant location and guide the user in creating a countersink location or placing anchoring screws such that the device to be implanted ends up in the desired/planned location. In a robotic procedure, system 10 may be configured to provide outputs that direct the robot (under surgeon supervision) to create the planned countersink at the desired location(s) of the planned impanation site.

Some examples of IMDs may include devices miniaturized enough to fit within the burr hole used to access the brain. For such devices, the various data and graphical image capabilities of system 10 may be combined with the trajectory entry point considerations, helping the surgeon pick an entry location that both minimizes the impact of the skull implant (cosmesis, structural integrity, removal of bone) and the risk on brain entry (avoiding vessels, gyri/sulci considerations, minimizing impact to eloquent regions of cortex).

System 10 may include graphical tools and information processing techniques that may be used in planning and executing cranial based implantation procedure involving IMDs configured to perform stimulation therapy and/or recording functions associated with a patient, and in some examples, may be used in conjunction with planning and/or implementing other cranial implants where tradeoffs must be made on multiple criteria and on a patient specific basis. The features and function associated with system 10 may help guarantee a high degree of patient satisfaction (e.g., with respect to cosmetic concerns addressed before surgery, predictable recharge and telemetry performance, etc.), an efficient surgical procedure (e.g., with respect to planned location, lead management, or tool/template selection complete before first incision), and low risk of surprises during the implantation procedure (e.g., discovering that a lead is too short or a bone too thin) or post op complications (e.g., high profile implantations that may lead to infection).

In addition, the surgeon may use the data and other information provided by system 10, including the graphical depictions provided by system 10, to determine what configuration of device or devices should be implanted for a particular patient. The available IMDs may incorporate a plurality of different configurations. The surgeon may select a suitable standard configuration, and adapt that configuration to the patient by bending, trimming, or otherwise adjusting the IMD to fit the patient. Use of one or more standard configurations may be more efficient, convenient, and economical in some examples compared to building custom IMDs from scratch for each patient.

System 10 may be configured to store any portion or all of the information, including graphical image information associated with the rendering and generation any of the graphical images displayed as a result of proposed implantation for one or more selected devices and for each specific patient, for example into database 24 and/or into computer memory included within workstation 32. This stored information may be later retrieved by the processing circuitry included within workstation 32, and further processed by any of the techniques described above or throughout this disclosure, for use in further planning and/or for use during an actual implantation procedure as guidance for persons, such as a surgeon, performing any part of the implantation procedure associated with a patient.

In other examples, wherein some portion of the implantation procedure may be performed as a robotic procedure, for example in the process used to form a recess in the skull of the patient at a selected implantation site (under surgeon direction and supervision), data including graphic image data and/or metrics generated and stored within system 10 related to the patient and/or the planned implantation process may be provided to one or more devices (not shown in FIG. 1) that are performing the robotic process for the purpose of guiding and controlling these devices (under surgeon supervision) before and/or during the portion of the process being performed by the devices. These capabilities allow the planning process associated with a proposed implantation procedure for a patient to occur before the time the implantation procedure is actually initiated, and also allow retrieval of data associated with the finalized plan, including graphical images of the skull, scalp, and/or selected medical devices, for display and for use in providing guidance during the actual execution of the implantation process.

Figure 2:
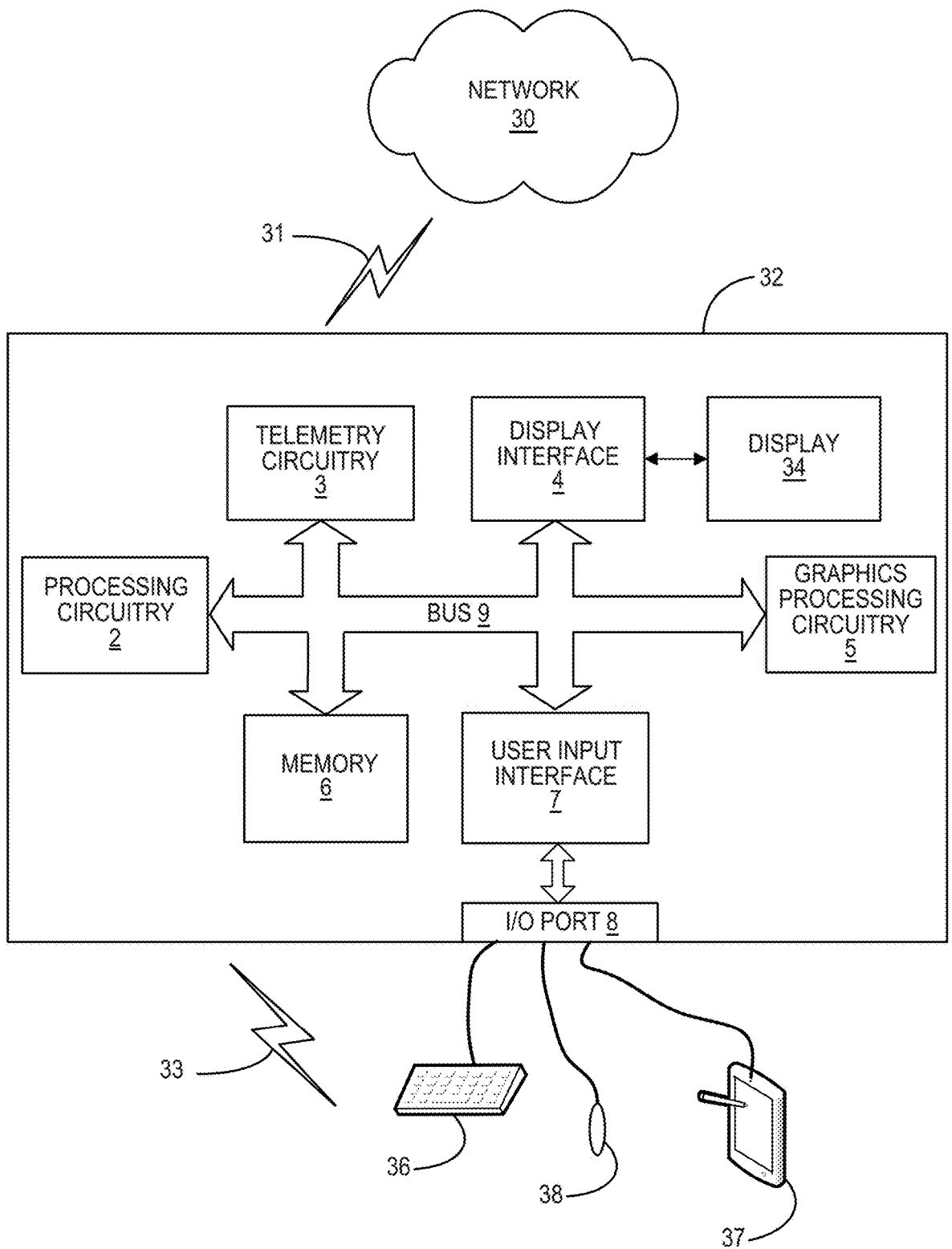
FIG. 2 is a block diagram illustrating an example of a workstation that may be used to implement the various techniques described this disclosure.

FIG. 2 is a block diagram illustrating an example of a workstation 32 that may be used to implement techniques described this disclosure. Workstation 32 may comprise a personal computer, a desktop computer, a laptop computer, a computer workstation, a wireless communication device (such as, e.g., a mobile telephone, a cellular telephone, a satellite telephone, and/or a mobile telephone handset), a handheld device such as a personal digital assistant (PDA), a mainframe computer or any other type of device that processes and/or displays graphical data.

As illustrated in the example of FIG. 2, workstation 32 includes processing circuitry 2, telemetry circuitry 3, a display interface 4 coupled to a display 34, graphics processing circuitry 5, electronic memory 6, and a user input interface 7 coupled to an input/output (I/O) port 8. Processing circuitry 2, telemetry circuitry 3, display interface 4, graphics processing circuitry 5, electronic memory 6, and user input interface 7 may communicate with each other using bus 9. Bus 9 may be any of a variety of bus structures, such as a third-generation bus (e.g., a HyperTransport bus or an InfiniBand bus), a second-generation bus (e.g., an Advanced Graphics Port bus, a Peripheral Component Interconnect (PCI) Express bus, or an Advanced eXentisible Interface (AXI) bus) or another type of bus or device interconnect. It should be noted that the specific configuration of buses and communication interfaces between the different components shown in FIG. 2 is merely exemplary, and other configurations of computing devices and/or other graphics processing systems with the same or different components may be used to implement the techniques of this disclosure.

Processing circuitry 2 may comprise one or more general-purpose and/or a special-purpose processor circuits that controls operation of workstation 32. Processing circuitry may include one or more processors, such as one or more microprocessors, application specific integrated circuits (ASICs), field programmable gate arrays (FPGAs), digital signal processors (DSPs), or other equivalent integrated or discrete logic circuitry.

Processing circuitry 2 may be configured to execute one or more software applications, such as programs stored in memory 6, to perform any of the functions and provide any of the features ascribed to workstation 32 throughout this disclosure, and any equivalents thereof The software applications that execute on processing circuitry 2 may include, for example, an operating system, a word processor application, an email application, a spread sheet application, a media player application, a graphical user interface application or another program that, when executed by the processing circuitry, provide one or any combination of the features and functions ascribed to workstation 32. For example, the software applications that execute on processing circuitry 2 may include accessing data associated with a patient and in some examples, patient population data, that may be stored in memory 6, and/or accessed through communication connection 31 and network 30 and stored in a device located externally to workstation 32, such as database 24 as illustrated and described with respect to FIG. 1.

Referring again to FIG. 2, processing circuitry 2 may utilize the accessed data to execute one or more graphics rendering instructions to cause the rendering of graphical data associated with any of the graphical illustrations, including any of the skull models, with or without the image annotation as described below, with respect to the skull of a specific patient, or for modeling of generic skull models. In various examples, the graphical data may be provided to graphics processing circuitry 5. Graphics processing circuitry 5 may include circuitry and/or additional software and/or processing circuitry that processes the graphical data, and provides data/and instruction to display interface 4 that allows display interface 4 to render a graphical image, such a three-dimensional image modeling the skull of a patient, at display device 34. The graphical data used in rendering the image display at display device 34 may include additional data, such as text data and/or menu selectable data, and/or image annotations that may be associated with the modeled image of the skull of the patient.

In some examples, the software instructions may conform to a graphics application programming interface (API), such as, e.g., an Open Graphics Library (OpenGL®) API, an Open Graphics Library Embedded Systems (OpenGL ES) API, an OpenCL API, a Direct3D API, an X3D API, a RenderMan API, a Weigel API, or any other public or proprietary standard graphics API. The techniques should not be considered limited to requiring a particular API.

In order to process the graphics rendering instructions, processing circuitry 2 may issue one or more graphics rendering commands to graphics processing circuitry 5 to cause graphics processing circuitry 5 to perform some or all of the rendering of the graphics data. In some examples, the graphics data to be rendered may include a list of graphics primitives, e.g., points, lines, triangles, quadralaterals, triangle strips, etc. used in the generating of the three-dimensional graphical images displayed by display device 34.

Memory 6 may store one or more programs, and may store data, such as patient data 14 and/or device data 20, and facilitates the transfer of programing and data going into and out of the memory. For example, memory 6 may receive memory read and write commands, and service such commands with respect to memory 6 in order to provide memory services for the components in workstation 32. Memory 6 may include one or more volatile or non-volatile memories or storage devices, such as, for example, random access memory (RAM), static RAM (SRAM), dynamic RAM (DRAM), read-only memory (ROM), erasable programmable ROM (EPROM), electrically erasable programmable ROM (EEPROM), flash memory, a magnetic data media or an optical storage media.

Memory 6 may store program modules and/or instructions that are accessible for execution by processing circuitry 2 and for graphics processing circuitry 5, and/or may store data for use by the programs executing on processing circuitry 2 and for graphics processing circuitry 5. For example, memory 6 may store user applications and graphics data associated with the applications. Memory 6 may additionally store information for use by and/or generated by other components of workstation 32. For example, memory 6 may act as a device memory for processing circuitry 2 and for graphics processing circuitry 5, and may store data to be operated on by processing circuitry 2 and/or graphics processing circuitry 5. For example, memory 6 may be configured to store data related to images, including three-dimensional graphical images of skull models that may include image annotations, and/or data input into workstation 32 by a user, all related to the planning, implementation, and guidance related to a cranial based implant procedure for a specific patient.

In some examples, memory 6 is a non-transitory storage medium. The term "non-transitory" indicates that the storage medium is not embodied in a carrier wave or a propagated signal. However, the term "non-transitory" should not be interpreted to mean that memory 6 is non-movable or that its contents are static. As one example, memory 6 may be removed from workstation 32, and moved to another device. As another example, memory, substantially similar to memory 6, may be inserted into workstation 32. In certain examples, a non-transitory storage medium may store data that can, over time, change (e.g., in RAM).

Telemetry circuitry 3 may be configured to receive and transmit, by wired connection or by telemetry, signals incoming to and outgoing from workstation 32. For example, telemetry circuitry 3 may be configured to provide and manage communications, illustrated by communication link 31, that occur between workstation 32 and network 30.

Input devices, such as a keyboard 36, a computer mouse 38, and/or a tablet 37 may be coupled to workstation 32 through I/O port 8, and allow a user to provide inputs to workstation 32. For example, text inputs may be provided to workstation 32 via inputs made to keyboard 36. Actuation, manipulation, and/or selection inputs may be provided to workstation 32 via inputs made using computer mouse 38. For example, movements and/or a continuously variable trackball type inputs provided through computer mouse 38 may be used to manipulate portions of the image(s) provided at display device 34, for example via manipulation of movement and selection using a computer cursor generated in the images provided at display device 34. Inputs to the computer mouse, such as actuation of a "clickable" component of the computer mouse, may be provided as inputs to the workstation 32 to allow a user to indicate a selection, and/or to manipulate (e.g., move, rotate, enlarge, or shrink) graphical features being displayed by display device 34. Tablet 37 may be used to provide inputs, such as selections of menu items provided on the tablet, or through other motions such as gesture motions made across the surface of the tablet to provide inputs to workstation, 32 for selection and/or manipulation of the of graphical images being displayed by display device 34. In various examples, one or more of keyboard 36, computer mouse 38, and/or tablet are wireless devices that communicate with workstation 32 via a wireless connection, such as a radio frequency (RF) or an infra-red (IR) technology, illustratively shown as communication link 33 in FIG. 2.

Figure 3A:
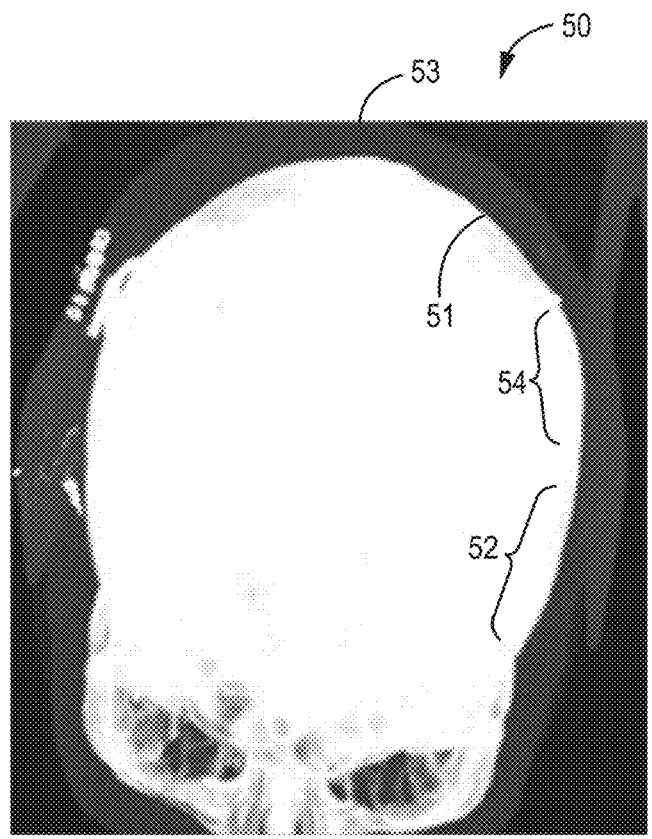
FIG. 3A illustrates an axial view an image associated with a head portion of a patient in accordance with the various techniques described in this disclosure.

FIG. 3A illustrates an axial view an image 50 associated with a head portion of a patient according to the various techniques described in this disclosure. In various examples, the image data illustrated in FIG. 3A may be generated, at least in part, by an image or images taken using one or more devices of the imaging equipment 12 as shown in FIG. 1, such as images generated by X-ray, MRI, CT, and fluoroscopy.

The image and the data associated with the image 50 as illustrated in FIG. 3A may be generated using both hard and soft tissue data. For example, image 50 may include hard tissue data related to the skull 51 of the patient. In addition, image 50 may include soft tissue data related to the scalp or brain 53 of the patient. A planning system, such as the FrameLink Stereotactic Planning System or the Stealth Station, both produced by and commercially available from Medtronic Surgical Navigation Technologies®, can combine hard-tissue and soft-tissue image data to generate a three-dimensional model of an imaged body part, such as the head of the patient. The imaging system integrates hard-tissue data, such as data from an x-ray or CT scan, with soft-tissue data, such as data from an MRI scan.

In various examples, one or more processors, as included for example in processing circuitry 2 of workstation 32, may process the image data to generate additional data associated with the image 50. For example, data representative of the exterior contours of skull 51 in image 50 may be further processed to determine an indication of the amount of curvature or relative flatness of various portions of the exterior surface of the skull. The exterior contours of skull 51 at the portion of the skull indicated by bracket 52 may be indicated in image 50, for example by arrows, color, or some of the form of graphical indication, as having a flatness that may be at or above some threshold flatness value.

As also illustrated in FIG. 3A, the exterior contours of skull 51 at the portion of the skull 51 as indicated by bracket 54 may by indicated in image 50, for example by arrows, color, or some other form of graphical indication, as having a curvature that is above, e.g., not as flat as compared to the threshold curvature value. The determination of curvature and/or flatness of portions of the skull 51 are not limited to any particular technique or techniques, and for example may be based on a comparison of the variation of the contour of a first point on the skull with a set of other points at some predetermined distance or distances from the first point relative to a plane that is tangent to the skull at the first point. A threshold curvature value and/or a threshold flatness value may be a programmable value that is stored into the system, such as saved in memory 6 workstation 32, and may be changed by inputs provided to the system, for example by inputs provided by user 40.

In various examples, the threshold value or values used to determine when a portion of the skull 51 is at or above some threshold curvature/flatness value may be determined based on a specified maximum contour of the skull that, for a given device, would allow for implantation of the device at that portion of the skull. In various examples, this threshold value may be different for different implantable devices, and may be programmable, for example set at some default or predetermined value initially, and may be manipulated by the user of the system, such as a user providing inputs to workstation 32. For example, a medical device being considered for implantation may comprise a case or housing having a substantially flat surface that would be oriented toward the patient when implanted. When considering this device, the modeling of the skull may include providing an indication of an area or areas of the skull that are or could be shaped, for example by cutting, to provide a flat area for mounting the device. In other examples, the medical device may comprise a case or housing having a curved surface that would be oriented toward the patient upon implantation of the device. In such instances, the modeling of the skull may include providing an indication of an area or areas of the skull that confirms to the curved shape of the device. In addition, a particular medical device may be available in a variety of different cases or housing that provide different radii or curvatures of their outside surface(s), and the modeling could include an indication of which one or ones of these devices might best fit various areas the skull of a particular patient. In various examples, the image data generated from image 50 may be used, in whole or in part, to generate three-dimensional data related to the skull and/or the scalp of the patient, and to provide data that may be used as various parameters, such as skull shape, size, curvature/flatness, and skull thickness parameters, to render images of the patient's skull and/or the patient's scalp, with or without superimposed image annotations, as further described below.

Figure 3B:
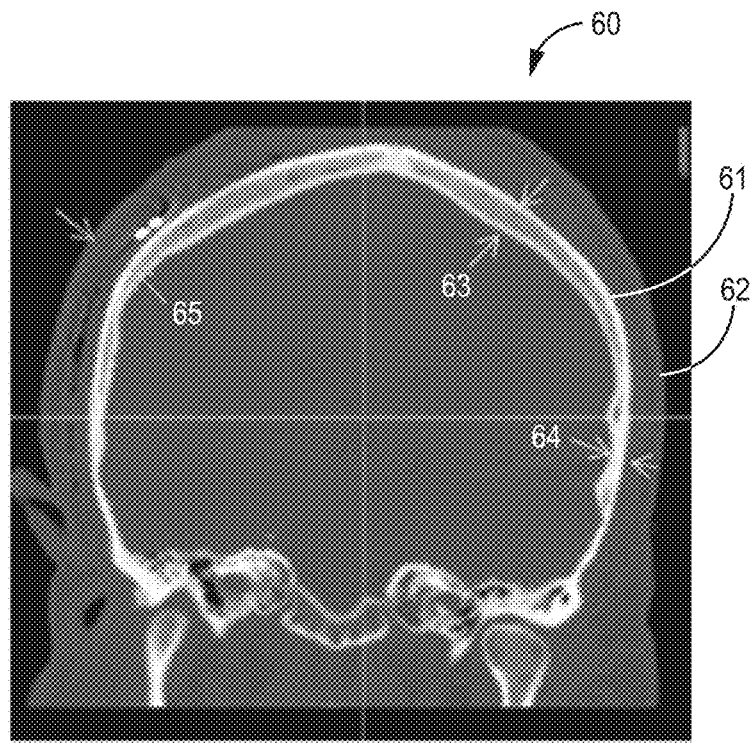
FIG. 3B illustrates a coronal view of an image associated with a head portion of a patient in accordance with the various techniques described in this disclosure.

FIG. 3B illustrates a coronal view of an image 60 associated with a head portion of a patient according to the various techniques described in this disclosure. In various examples, the image data illustrated in FIG. 3B may be generated, at least in part, by any images taken using one or more devices of the imaging equipment 12 as shown in FIG. 1, such as images generated by X-ray, MRI, CT, and fluoroscopy. The image and the data associated with the image 60 as illustrated in FIG. 3B may be generated using both hard and soft tissue data. For example, image 60 may include hard tissue data related to the skull 61 of the patient. In addition, image 60 may include soft tissue data related to the scalp 62 of the patient. An imaging system, such as the FrameLink™ Stereotactic Planning System, produced by and commercially available from Medtronic Surgical Navigation Technologies, can combine hard-tissue and soft-tissue image data to generate a three-dimensional model of an imaged body part, such as the head of the patient. The imaging system integrates hard-tissue data, such as data from an x-ray or CT scan, with soft-tissue data, such as data from an MRI scan.

As shown in FIG. 3B, image 60 illustrates data related to the skull 61 and to the scalp 62 of a head of a patient taken at some cross-sectional plane that is perpendicular to a longitudinal axis of the patient running from the top of the patient's head toward the patient's neck. A thickness of the skull 61, as illustrated by the portion of the skull between arrows 63, may be measured, and a thickness value of the skull determined for that portion of skull 61. Other thickness values may be determined for various portions of the skull 61, for example as illustrated for the portion of the skull 61 located between arrows 64 in image 60. The number of positions where the thickness value for skull 61 may be determined is not limited to any particular positions and/or to any number of positions, and may be any number positions along the skull 61 as shown in image 60 as deemed appropriate to provide the image data to be use by the system for rendering images as described throughout this disclosure.

In addition to any determinations related to the skull thicknesses of skull 61, other image data associated with the thickness of the scalp of the patient at various portions of skull 61 may be determined. As shown in FIG. 3B, a thickness of the scalp of the patient, as illustrated by the portion of the scalp located over the skull 61 between arrows 65, may be measured, and a thickness value of the scalp 62 determined for that portion of skull 61. Other thickness values associated with the thickness of the scalp 62 at various portions of skull 61 may be determined using data included in image 60. The number of positions where the thickness value for scalp 62 may be determined is not limited to any particular positions and/or to any number of positions, and may be any number of thicknesses associated with scalp 62 at positions of the skull 61 as shown in image 60, as deemed appropriate to provide the image data to be use by the system for rendering images as described throughout this disclosure.

As would be understood by one of ordinary skill in the art, image 60 as shown in FIG. 3B illustrates image data from one slice taken in cross-section of the head of a patient, and several other images including data taken from difference slices imaged at different cross-sectional portions of the patient's head are possible. In various examples, the image data from multiple slices from a same patient's head may be combined to generate three-dimensional data related to the skull and/or the scalp of the patient. This three-dimensional data may be used, in whole or in part, to generate the three-dimensional graphical images, and to provide data that may be used as the various parameters, such as skull shape, size, curvature/flatness, and skull thickness parameters, to render images of the patient's skull and/or the patient's scalp with or without superimposed image annotations, as further described below.

Figure 4:
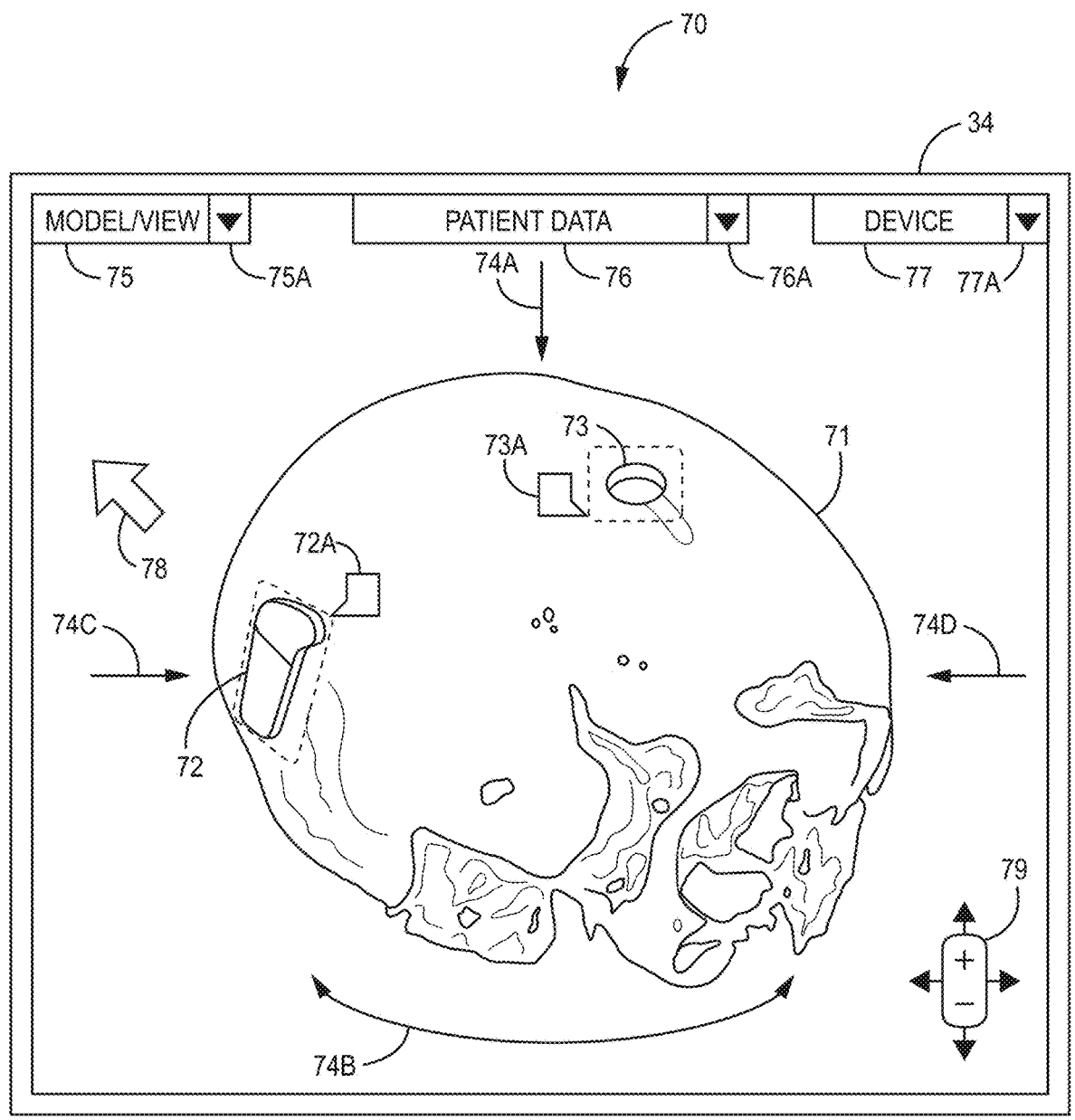
FIG. 4 illustrates an example three-dimensional image generated and displayed in accordance with the various techniques described in this disclosure.

FIG. 4 illustrates an example three-dimensional image 70 generated and displayed in accordance with the techniques described in this disclosure. As shown in FIG. 4, image 70 includes a three-dimensional (3D) image of a skull model 71 of a patient. The three-dimensional image may be generated by processing circuitry (such as processing circuitry 2 and/or graphics processing circuitry 5 illustrated and described with respect to FIG. 2), and rendered as image 70 on a display device 34 of a workstation, such as workstation 32 shown and described with respect to FIG. 1.

As shown in FIG. 4, the three-dimensional image of skull model 71 may be generated from a combination of data generated by imaging devices, such as imaging equipment 12, data stored in a database such as database 24 as illustrated and described with respect to FIG. 1, and/or using data stored in local memory, such as memory 6 of the workstation 32 coupled to display device 34. In various examples, the image of skull model 71 may be generate based on data that is specific to a particular patient. In other examples, the image of skull model 71 may be generated based on data associated with a hypothetical patient, for example based on a model of a hypothetical patient using generalizations associated with the skull of a typical patient of a predefined gender, age, size, and/or other parameters associated with a typical patient having a same or similar set of characteristics. In some cases, the generalizations for the hypothetical patient may be obtained from patient population data for patients having similar characteristics (age, size, gender) as the current patient.

As shown in FIG. 4, the image of skull model 71 provides a three-dimensional graphical representation of a perspective view of the side and partial portions of the top and front of a skull. In various examples, the three-dimensional image of skull model 71 may be manipulated to be rotated or otherwise re-oriented so that the view provided as image 70 illustrates skull model 71 viewed from different viewing angles and/or perspectives. For example, the image of skull model 71 may be manipulated so that the view of skull model 71 is shown from a direction looking more directly at the top of skull model 71, as indicated by arrow 74A. The image of skull model 71 may also be rotated in a right or left orientation, as indicated by curved arrow 74B, to allow the viewing angles around the perimeter of skull model 71 to be provided in image 70. Rotation of the viewing angles may allow image 70 to provide an image of skull model 71 looking more toward the back side of the skull, as indicated by arrow 74C, more toward the front side of skull model 71 as indicated by arrow 74D, or a view looking toward the side of skull model 71 opposite the side visible in image 70 as shown in FIG. 4.

The image 70 may include the ability to enlarge the skull model 71 as displayed (zoom in function), or to make the image of skull model 17 smaller, smaller (zoom out function), and to navigate so that a center of image 70 is located as different portions of three-dimensional image of skull 71, all based for example on user provided inputs. In various examples, image 70 includes an actuatable graphic or set of graphics 79 (e.g., directional/rotational arrow, plus/minus zoom controls), that may be actuated using inputs, for example provided by a user, to manipulate cursor 78 with respect the graphic 79 that allow the user to provide inputs to the system rendering and displaying image 70 so that image 70 may be manipulated in any of the manners described above.

Image 70 may include one or more additional data fields 75, 76, 77, displayed on display device 34 as part of image 70. In some examples, data field 75 may be provided as a selectable menu including a selectable pull-down button 75A that allows a user to select, for example using a movable computer-generated cursor 78 provided as part of image 70, the pull-down button 75A to cause image 70 to display one or more options for the viewing parameters to be provided as part of image 70. For example, when actuated, the pull-down button 75A may cause image 70 to generate and display a series of viewing options related to the three-dimensional image of skull model 71 being provided as part of image 70. Various views of interest may be provided as one or more "default views" that may be available for rendering by the display when selected as a menu option provided by pull-down button 75A. These default views may include but are not limited to a view orthogonal to the top surface (e.g., looking down at the top of the skull), a view parallel to a cross section (e.g., sliced through the long axis of the skull, showing for example depth of countersink vs device thickness), and a view tangent to the skull (showing for example excursions of the profile outside of the skull). The viewing options may include options to display or not display various image annotations that may be superimposed onto the image of skull model 71. Image annotations may include some type of graphical indication, such as arrows, colors, boundary lines, text, or some other form of graphical indication, that may be superimposed onto the three-dimensional image of skull model 71. The image annotations may be related to various data parameters and or evaluation parameters associated with the patient and/or the skull model 71 being graphically illustrated as image 70. These parameters may be associated for example with skull thicknesses, dimensions related to skull size, skull shape, or other parameters described throughout this disclosure related to the skull model 71 or to a patient associated with the skull model 71.

For example, numerical or color indications and/or boundary line indications may be provided as image annotations superimposed onto the image of skull model 71 that are related to evaluation parameters, such as skull thickness, skull size or shape, and/or skull curvature/flatness relative to curvature/flatness threshold value or values. These image annotations may be tuned on or turned off with respect to the graphical image that is provided as part of the display provided as image 70 by selecting and/or unselecting the various menu options provided by actuation of the pull-down button 75A. In other examples, the display options provided when the pull-down button 75A is actuated may include options to turn on and to turn off the display of data related to soft tissue, such as scalp thickness, blood vessel distribution, and/or location, and nerve location indications related to the patient associated with the graphical image of the skull models being provided as part of image 70. For example, as noted above one of the considerations for blood vessels may be regarding the incision used as part of the implant procedure. As part of modeling an implantation procedure, the system may visualize direction of dominant vessel flow (for example based on a contrast enhanced imaging—where contrast agents are injected to help vessels show up on imaging) and then provide feedback/suggestions as to which direction to make the incision to minimize disruption to the blood vessels during and as a result of the implantation procedure. Other options that may be provided as part of a menu provided by actuation of the pull-down button 75A include options to turn on and to turn off the display of data related to maximum and/or minimum areas of separation between a first location for a selected IMD and one or more other proposed implantations of additional IMDs.

Data field 76 may be included in image 70, and may be configured to display patient data, such as a name and/or biographical information related to a patient, such gender, age, and/or contact information such as an address, phone number and/or email information associated with the patient. Data field 76 may include medical data, such as medical history and current medical conditions and/or medications that are current being taken or have been previously associated with the patient. In some examples, data field 76 includes an actuatable pull-down button 76A, that when actuated provides a menu listing of one or more patients that have data available in the system providing the image 70. Upon actuation of the pull-down button 76A, the listing of patients may be graphically illustrated in image 70, and may be configured to allow a user to select, for example using cursor 78, one of the patients from the list. Upon selection of a patient for the list, the system providing image 70 may be configured to go search for and retrieve any data available to the system related to that patient, and to render images, such as skull models, for the patient based on the available data associated with that patient.

In various examples, data field 76 is a fillable data field that is configured to allow a user to input data into data field, wherein the input data may be used to control the rendering and display of the image provided as image 70. For example, a patient name or patient identification number may be input into the data field 76, for example by selecting data field 76 using cursor 78, and then typing information into the selected text field for example using a keyboard 36 or using a tablet 37, as illustrated and displayed with respect to FIG. 2. Referring again to FIG. 4, upon receiving the patient name or other patient identification information at data field 76, the system generating and displaying image 70 may search memory and/or databases, and access any data, including image data associated with the patient, based on input of the patient information. In some examples, the data provided as inputs to data field 76 is used to link the image(s) generated as image 70 to a particular patient, allowing a user to access image data associated with a patient the user would like to view and/or further work with. In various, examples, data field 76 is configured to allow a user, such as a surgeon, to add data as inputs to data field 76, such as notes regarding possible procedures that may be performed on the patient as part of an implantation planning process, and to have the data stored for later access in association with the patient and/or with the image being provided as image 70.

Data field 77 may be included in image 70, wherein data field 77 may be associated with one or more medical devices, such as implantable medical devices, that may be implanted or otherwise attached to a skull of a patient, and configured to provide monitoring and/or therapy to the patient once installed. An example of such as device is illustrated as device 72 in FIG. 4 as being implanted on a lower portion of the image of skull model 71. In various examples, device 72 is one of a plurality of devices that may be selected using a pull-down button 77A associated with data field 77. In various examples, actuation of the pull-down button 77A may cause image 70 to provide a menu as part of image 70 that lists various devices that may be used by the system for modeling an implantation on the skull of a patient. Selection of a particular device from the menu provided by the actuation of pull-down button 77A may cause the system that is rendering and providing image 70 to retrieve data, such as device data 22, associated with the selected device, and to generate an image of the device in a same scale and having dimensions that correspond to the scale of the image of skull model 71.

The generated image of the selected device may be manipulated within image 70 to allow the image of the selected device to be placed at various locations on the exterior surface, or in some examples within a recessed area of the image of skull model 71. In various examples, the device, such as device 72 as shown in FIG. 4, may be selected within the image provided by image 70, and when selected, may then be manipulated, for example using cursor 78, to move, reposition, and/or reorient the image of the selected device 72 relative to the position of skull model 71. As such, image 70 allows for rendering of a variety of images displaying device 72 positioned at different locations and/or different orientations, with and/or without some amount of recess of the device 72 with respect to the exterior surface of the image of skull model 71, based on inputs provided to the system providing image 70.

In various examples, using the pull-down button 77A allows inputs related to a selection of a different device other than a currently display device such as device 72, to be generated as part of image 70. In some examples, the rendered image of the different device may be generated in the image, wherein the newly selected device replaces the image of the existing device in image 70, such as existing device 72 as shown in FIG. 4. In other examples, the selection of one or more devices using the pull-down button 77A allows images of the one or more addition selected devices to be added to the image 70, while retaining the rendered image of the device or devices already displayed in image 70. This feature allows multiple devices to be selected and displayed at a same time in a graphical image of a skull model, such as skull model 71, to be provided as image 70. In any case, the newly selected devices may be manipulated through inputs provided to the system, for example using cursor 78, to allow a user to move, position, and/or reorient the newly selected device(s) in a same or similar manner as described above with respect to device 72.

Data field 77 may also be configured to allow inputs to the system providing image 70, for example inputs provided by a user, that may be related to new devices not previously available for selection through the pull-down menu provided through the actuation of pull-down button 77A. Data field 77 may also be configured to allow inputs to the system providing image 70 related to devices that may be associated with the specific patient that is associated with the image of skull model 71 provided as part of image 70. For example, a user such as a surgeon may add notes or other information associated with one or more of the devices associated with the data provided in data field 77 and the specific patient associated with the image of skull model 71 being generated at image 70. For example, a user may provide inputs related to the desirability or potential issues that may be associated with the use of a particular one of devices 22 having data that is accessible through accessing data fields 77 and linked to the specific patient associated with the skull model 71. For example, a user such as a surgeon may model a particular device 22 using the graphical image 70 and skull model 71, then may provide inputs, such as notes, comments, and/or observations regarding the modeling session and/or the particular device 22 into data field 77 so that the inputs become associated with the particular device 22 and the particular patient associated with skull model 71. In this way, the user may record for later retrieval information associated with a particular modeling session performed using data associated with a specific patient. Data inputs to data field 77 may be accomplished at least using any of the techniques described above with respect providing inputs to system 10.

In some examples portions of the skull model as provided in image 70 may be selectable, and when selected the system providing image 70 may provide additional information and/or perform additional functions based on the selection. By way of example, as dashed box 73 is shown in image 70 surrounding a portion of the skull where a burr hole with a recess is illustrated. Dashed box may be configured as a selectable portion of image 70, and when selected, the system providing image 70 may be configured to illustrate additional information, such as text included in a pop-up box 73A, that is associated with the selection item (e.g., the burr hole).

In some examples, selection of the graphical image includes selection of a device illustrated in image 70, such as device 72. In some examples, selection of a device in image 70 causes image 70 to display of a pop-up box 72A that may include additional information associated with device 72, such as manufacturer's data for device 72, and/or other data, such as comments and remarks related to device 72 that were entered into the system by a user, such as a surgeon. Selection of device 72 may be accomplished by a user providing inputs to the system providing image 70 to manipulate cursor 78 to position the cursor and actuate the cursor to select device 72 within image 70. In some examples, the system providing image 70 is configured to allow a user, such as a surgeon, to add information, such as comments, or notes, to the pop-up box, and to have the information saved so that the added information may be retrieved and displayed at some later time when selection of the device 72 is again made.

In some examples, information associated with feature of the skull, such as an existing burr hole, is included in the patient data associated with skull model 71. Selection of the dashed box 73, for example using cursor 78, in some examples causes the system providing image 70 to search and retrieve data associated with the feature(s) of dashed box 73, such as patient history, current status and past usage of the selected feature, and provides the information, for example as text illustrated on the display device 34, as a pop-up box 73A displayed in the image 70 near the selected feature. In some examples, the system providing image 70 is configured to allow a user, such as a surgeon, to add information, such as comments, or notes, to the pop-up box, and to have the information saved so that the added information may be retrieved and displayed at some later time when selection of the dashed box 73 is again made.

These selectable features associated with certain portions of an image being provided at display 34 may be available and provided in association with image 70, or any other images described in this disclosure, and are not limited to any particular feature displayed in these images. These selectable features are also not limited to features being displayed on the actual graphical image of the skull models described in this disclosure, and may include other features that are rendered and graphically displayed as part of the images provided at display device 34, or any equivalents thereof.

Figure 5A:
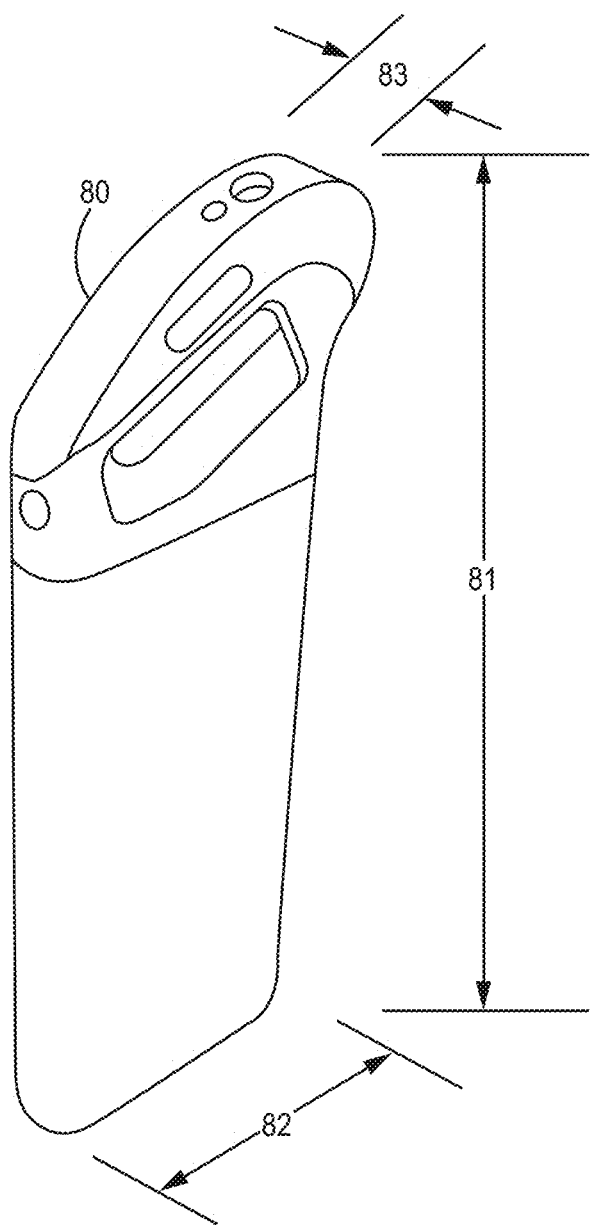
FIG. 5A illustrates a perspective view of an example implantable medical device that may be modeled for implantation for a patient in accordance with the various techniques described in this disclosure.

FIG. 5A illustrates a perspective view of an example implantable medical device 80 that may be modeled for implantation for a patient in accordance with the techniques described in this disclosure. As shown in FIG. 5A, medical device 80 comprises a device having a substantially flat rectangular shaped housing, that may be designed for implantation to an exterior surface of the skull of a patient, or may be implanted partially or wholly within a recess formed in some portion of the skull of a patient.

Device 80 in some examples has an overall length dimension 81 having a value in a range of 25 to 50 mm, an overall width dimension 82 having a value in a range of 10 to 20 mm, and a thickness dimension 83 having a value in a range of 3 to 6 mm. Device 80 may include electrical circuitry configured to provide electrical stimulation therapy, such as DBS therapy, and/or to monitor electrical signals such as neurological signals of the patient, in general thru the electrodes coupled to device 80 through one or more leads. The electrodes couple to device 80 may be positioned at a target structure, such a one or more brain tissues of the patient, and electrodes coupled to device 80 through the one or more leads. The lead or leads coupling device 80 with the electrodes may be physically routed from one or more connector blocks of device 80 through an area under the scalp of the patient in the area of the device 80 to one or more burr holes in the skull of the patient skull through which the lead or leads pass. Device 80 may be an example of a device having data associated with the device stored on or otherwise accessible to a system, such as system 10 as illustrated and described with respect to FIG. 1, and that may be rendered and displayed as a graphical image for use in modeling the device in proposed implantations associated with the skull models as described throughout this disclosure. For example, using data associated with device 80, a graphical image of the device may be rendered for example as device 72 shown in image 70 of FIG. 4, and may be manipulated and modeled according to any of the techniques described in this disclosure related to IMDs and modeling of implantations using IMDs.

Device 80 as illustrated and described with respect to FIG. 5A is an example of the type of device that may be modeled using the devices, systems, and techniques described throughout this disclosure. However, the types of devices that may be modeled by the devices, systems, and techniques described throughout this disclosure are not limited to any particular device, and may include implantable medical devices that have shapes, overall dimensions, and other features that are different from those described and illustrated with respect to device 80. For example, device 80 is described as having a flat rectangular shaped housing. Other devices that may be modeled by the devices, systems, and techniques described throughout this disclosure may include a substantially flat device having flat surfaces forming a front and back sides of the device that are parallel to one another, and that have a circular or semicircular shaped sidewall coupling the outside perimeters of the flat side surfaces of the device. In other examples, one or more of the front and back surfaces of an implantable device may include a three-dimensional curvature of one or both of these surfaces. In other examples, the device itself may be flexible so as to be bendable along one or more axes of the device. For any examples of implantable devices, the devices, systems, and techniques described throughout this disclosure may be configured to use data associated with the device so that a graphical image of the device may be rendered, for example as device 72 shown in image 70 of FIG. 4, and may be manipulated and modeled according to any of the techniques described in this disclosure related to IMDs and modeling of implantations using IMDs.

Figure 5B:
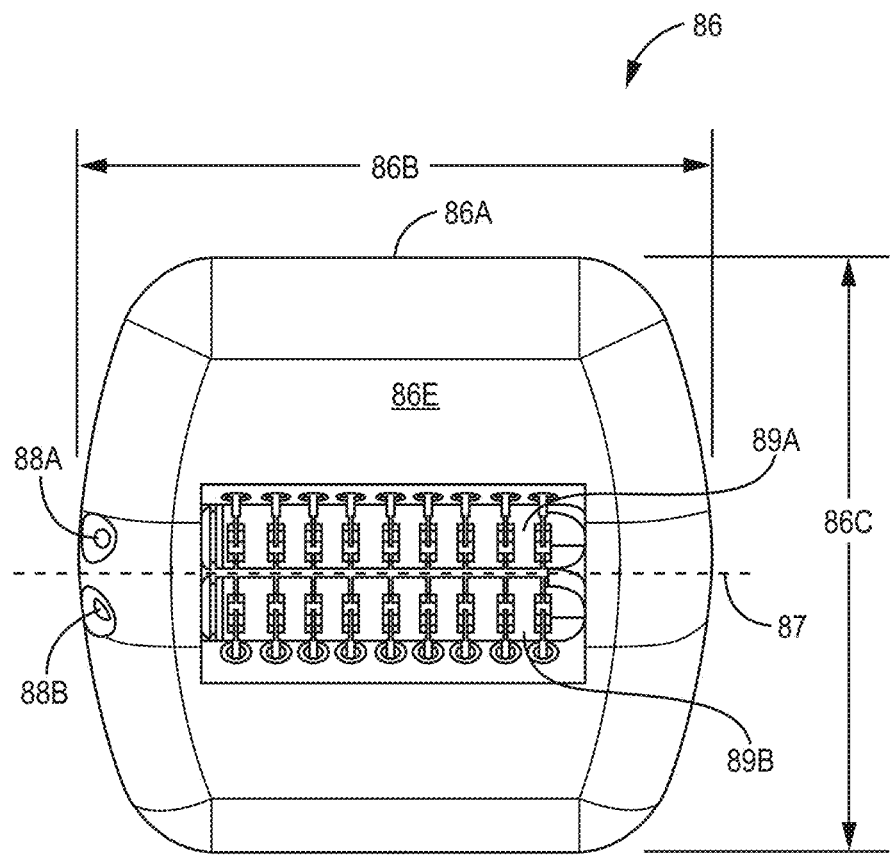
FIG. 5B illustrates a top view and a side view of another example implantable medical device that may be modeled for implantation for a patient in accordance with the various techniques described in this disclosure.
Figure 5B:
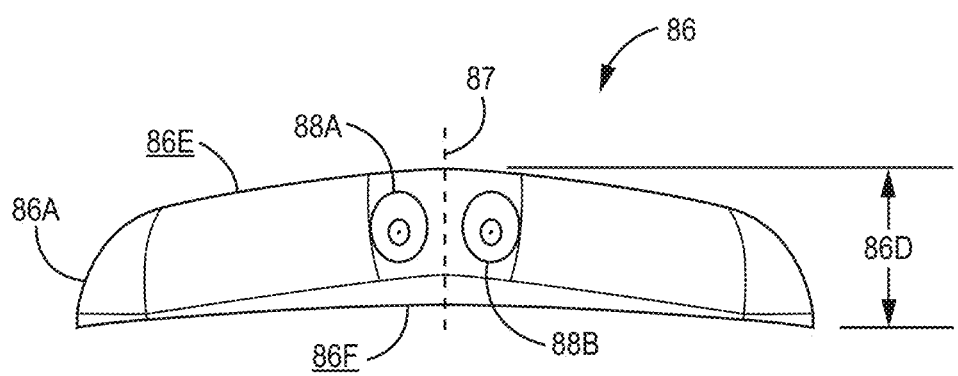

FIG. 5B illustrates a top view and a side view of another example implantable medical device 86 that may be modeled for implantation for a patient in accordance with the various techniques described in this disclosure. As shown in FIG. 5B, medical device 86 comprises a device housing 86A having a top surface 86E comprising one or more sloped surfaces that may slope away and downward toward a bottom surface 86F of device 86 as these top surfaces extend away from a center line 87 of the device. An outer perimeter of the device 86 may comprise a rectangular or square-shaped housing perimeter having one or more side surfaces having a curved or arc shape when viewing device 86 looking toward the top surface 86E. Device 86 may have a width dimension 86B in a range of 34 to 40 millimeters (mm), a height dimension in a range of 35 to 40 mm, and a maximum thickness dimension 86D in a range of 7 to 10 mm. In some examples device 86 may have a width dimension 86B of 34.3 mm, a height dimension 86C of 35.5 mm, and a thickness dimension 86D of 8.1 mm. Examples of device 86 are not limited to devices having these dimensions or ranges of dimensions, and examples of device 86 may include devices having one or more dimensions that are smaller or larger than the dimensions described above.

Device 86 that may be designed for implantation to an exterior surface of the skull of a patient, or may be implanted partially or wholly within a recess formed in some portion of the skull of a patient. In various examples, bottom surface 86F may be placed in contract with the skull of the patient, or may be placed in contact with a bottom surface of a recess formed in the skull in the patient as part of a proposed implantation of device 86. The sloped surfaces of top surface 86E of device 86 may be positioned so that the top surfaces are opposite the side of device 86 that is to be placed in contact with the skull of the patient. The sloped surfaces of top surface 86E may provide a shape that better conforms, at least to some extent, to the curvature of the area of the skull where device 86 is being considered for implantation, and thus may provide an implanted device that extends less and/or is less visually obvious after implantation due to the sloped surfaces conforming somewhat to the curvature of the patient's skull. In some examples, bottom surface 86E is also curved to better conform to the curvature of the skull of a patient in the area of the skull where device 86 is to be implanted. In other examples, the bottom surface 86E is flat, and conforms to a flat surface formed as the bottom surface of a recess formed in the skull of the patient that is to receive the device 86 as part to the impanation procedure.

As shown in FIG. 5B, device 86 may be substantially mirrored relative to the portions of the device provided on each side of central line 97, each half of device 86 providing one of two channels defined as channels 88A and 88B. Each channel may be on either side of center line 97. Channel 88A may comprise a coil 89A coupled to a plurality of electrical contacts and to the electrical circuitry housed within device 86. Similarly, channel 88B may comprise a coil 89B coupled to a plurality of electrical contacts and to the electrical circuitry housed within device 86. In some examples, the electrical circuitry coupled to channel 88A is electrically isolated from the electrical circuitry coupled to channel 88B. In some examples, one or more portions of the electrical circuitry, such as but not limited to a power source included within device 86, may be shared by the electrical circuitry coupled to the first and second channels 88A, 88B. As a result of having two channels 88A and 88B, device 86 may be configured to simultaneously provide therapy to and/or to monitor a patient through two separate leads (not shown in FIG. 5B) coupled to channels 88A and 88B, respectively.

Figure 6:
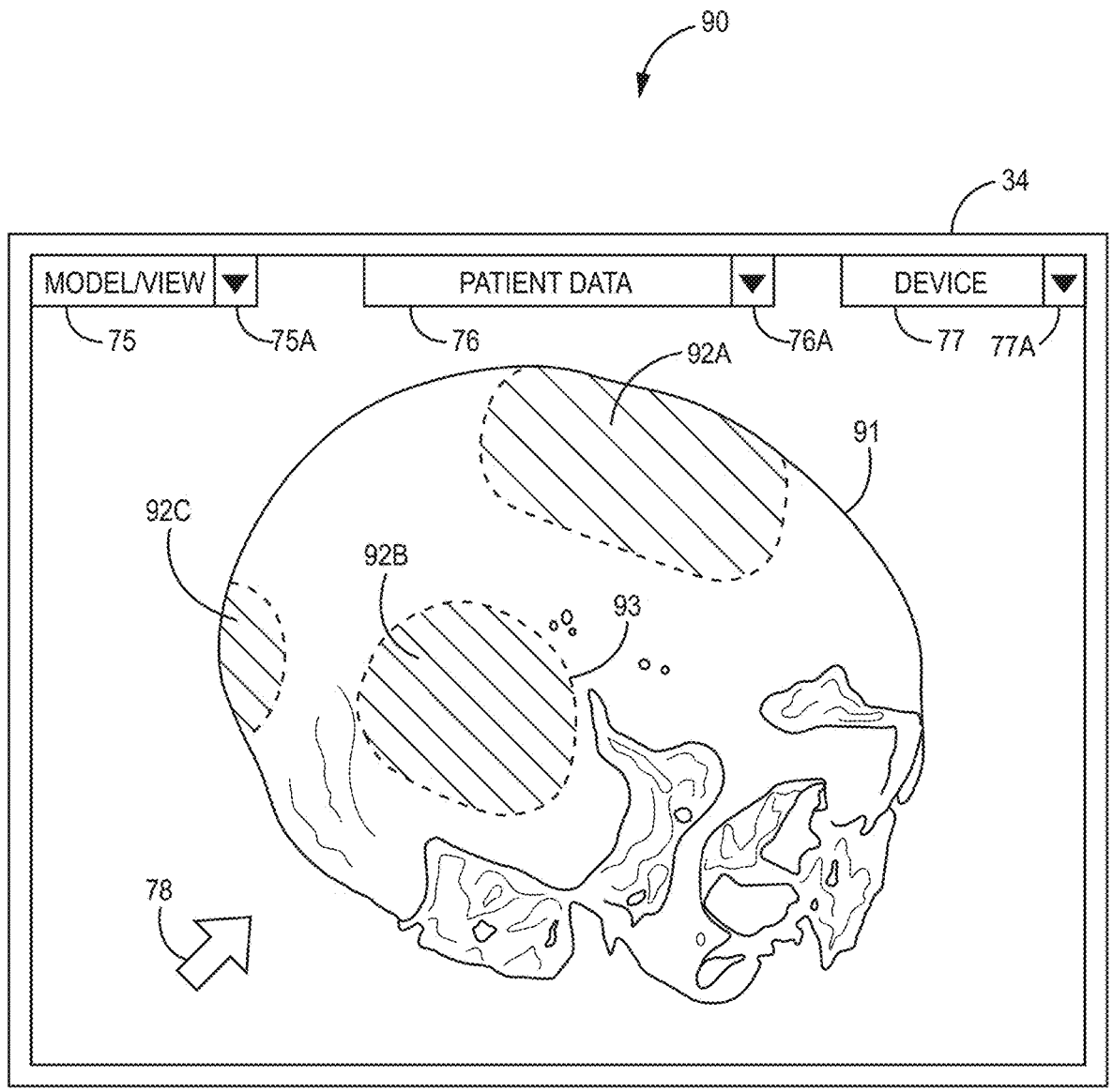
FIG. 6 illustrates an example three-dimensional image generated and displayed in accordance with the various techniques described in this disclosure.

FIG. 6 illustrates an example three-dimensional image 90 generated and displayed in accordance with the techniques described in this disclosure. As shown in FIG. 6, a three-dimensional image of a skull model 91 of a patient is rendered and displayed on display device 34. The three-dimensional image of skull model 91 may be generated using any of the techniques and may be configured to provide and/or perform any of the features and functions associated with the image of skull model 71 as illustrated and described above with respect to FIG. 4. The graphical display of image 90 as illustrated in FIG. 6 may include the model/view data field 75, the patient data field 76, and/or the device data field 77 as described above with respect to FIG. 4, and may provide any combination of and/or all of the features and functions described above as ascribed to data fields 75, 76, and 77, and the associated pull-down buttons.

As shown in FIG. 6, the rendering of the image of skull model 91 includes the addition of image annotations defining areas 92A, 92B, and 92C, wherein each of areas 92A, 92B, and 92C is superimposed on the image of the skull model 91, and encloses or partially encloses an area on the exterior surface of the image of skull model 91. In various examples, the areas enclosed or partially enclosed by each of areas 92A, 92B, and 92C may designate areas of the skull model 91 that meet particular criteria, which may be based on one or more evaluation parameters. For example, an evaluation parameter associated with areas 92A, 92B, and 92C may be skull thickness, and the determination of the areas to be included in areas 92A, 92B, and 92C may represent areas of the skull modeled as skull model 91 that have a minimum skull thickness within the portion of the skull indicated by these areas in image 90. Thus, the evaluation parameter for areas 92A, 92B, and 92C is skull thickness, and the criteria that may be used to determine which portions of the skull model 91 are to be designated as areas 92A, 92B, and 92C may be areas that have at least a minimum skull thickness that may be specified by a user or determined in another way. The designation of these areas may be important in that these areas may represent areas of the skull that may be suitable for consideration as a possible implantation and/or fixations sites for one or more IMDs.

The evaluation parameter or parameters used to evaluate areas of the skull are not limited to skull thickness, or to any particular parameter(s), and may include other parameters such as skull size, skull shape including curvature/flatness of the skull in different portion of the skull, scalp thickness in the area of different portions of the skull, minimum and/or maximum separation distances that may be required between multiple implanted device, the location and/or condition of the hair of the patient, the location or strength of brain signals to be recorded, and the distribution of blood vessels and/or nerves in the scalp of the patient. In some examples, each different evaluation parameter will have a different defined criterion or set of criteria that is associated with the evaluation parameter. For example, the criteria associated with skull thickness may be based on a comparison of a skull thickness in an area of the skull model compared to a threshold thickness value, criteria associated with scalp thickness may be a threshold thickness value for the scalp, criteria associated with brain signals might be strength or orientation of recording vector, and criteria associated with the separation of multiple devices implanted on a same skull may be a threshold distance.

In various examples, the determination associated with areas that qualify and thus are rendered in image 90 as areas 92A-92C may be based on an evaluation of criteria for a single evaluation parameter, such as skull thickness, or may be evaluated using appropriate criteria for each of a plurality of evaluation parameters. When using multiple evaluation parameters, the areas illustrated in image 90 as areas 92A-92C may be areas of the skull that meet the criteria defined, respectively, for each to the evaluation parameters defined for the particular rendering and display of the image being provided by image 90.

The areas 92A-92C indicated in image 90 as meeting particular criteria based on one or more evaluation parameters may be graphically indicated in image 90 in some examples using a color, such as a green coloration, within the areas that are determined to meet the predefined criteria for the evaluation parameter or parameters. In various examples, the areas 92A-92C may include a boundary line, such as boundary line 93 illustratively shown as encircling the area 92B, that may be used in addition to or instead of the color described above to indicate the portions of the skull that enclose or partially enclose the areas determined to meet the predefined parameter(s).

In various examples, the evaluation parameters and/or the criteria used to define areas 92A-92C may be adjusted, for example by changing a threshold value used as criteria for the evaluation of at least one evaluation parameter, or for example by changing the evaluation parameter or the set of evaluation parameters used to determine which areas of the skull in the image of skull model 91 would be included as areas 92A-92C in image 90. Upon receiving inputs related to adjustments, additions, and/or deletions to the evaluation parameters and/or to the criteria used in the evaluation of the evaluation parameter(s), as may be supplied by a user or obtained in another way, the system rendering image 90 may be configured to re-render image 90 based on the adjusted evaluation parameters and/or the adjusted criteria, and to refresh the image 90 to illustrate the adjusted and/or new area or areas that may comply with the redefined evaluation parameters/criteria. Using this feature, the system provides a user with the ability to better model various factors that may impact a proposed or planned implantation procedure, and to also allow comparisons of various scenarios based on different evaluation parameters or different sets of evaluation parameters having various ranges and thresholds, to help optimize the implantation and the implantation process for the patient under consideration.

As an example, an evaluation parameter used to determine the areas to be includes as areas 92A-92C in image 90 may be based on areas of the skull illustrated as skull model 91 that have a skull thickness of at least some threshold thickness value. Based on the value assigned as the threshold thickness value, the image of skull model 91 may be rendered to indicate the areas 92A-92C that include areas of the skull having at least a skull thickness value equal to or thicker than the threshold thickness value. The system used to render and provide image 90 may be configured to allow a user to change the threshold thickness value, for example using data entry via data field 75, and actuate the system to re-render the image annotations previously indicated as areas 92A-92C to illustrate the areas of skull model 91 that qualify as having a skull thickness value the meets or exceeds the newly provided thresholds thickness value. As such, the system allows a user to provide inputs to the system to manipulate the evaluation parameters and/or threshold value(s) for the evaluation parameters associated with the image annotations illustrated with image 90, and to have the system re-render the image of skull model 91 based on the revised evaluation parameters/threshold values. These features allow a user, such as a surgeon, to explore and consider a variety to parameters and threshold limits as part of an implantation planning procedure in general and/or for a specific patient associated with the image data used to generate the image of skull model 91.

In addition, the areas 92A-92C may also be rendered as selectable areas within image 90, and may be selected, for example using cursor 78, in a manner similar to that described above with respect to the selectable portions of image 70 and FIG. 4, such as device 72 and dashed box 73. Referring again to FIG. 6, in some examples when one or more of areas 92A-92C is selected, image 90 may display additional information, such as information used as the current evaluation parameter or set of evaluation parameters, and information about the criteria used to evaluate the evaluation parameters that resulted in the determination of what areas would be indicated as areas 92A-92C in image 90. In some examples, the display of image 90 may be configured so that when one or more of areas 92A-92C is selected, a user may provide inputs to the system providing image 90 that modify which evaluation parameter or evaluation parameters are used, and/or to modify the criteria values used to evaluate the evaluation parameter(s) defining the areas 92A-92C. Based on these inputs, the system providing image 90 may be configured to re-render image 90 and so that areas 92A-92C that may appear on skull model 91 are indicative of areas of the skull model that meet the revised evaluation parameter(s) and/or the revised criteria used to evaluate the evaluation parameters.

Figure 7:
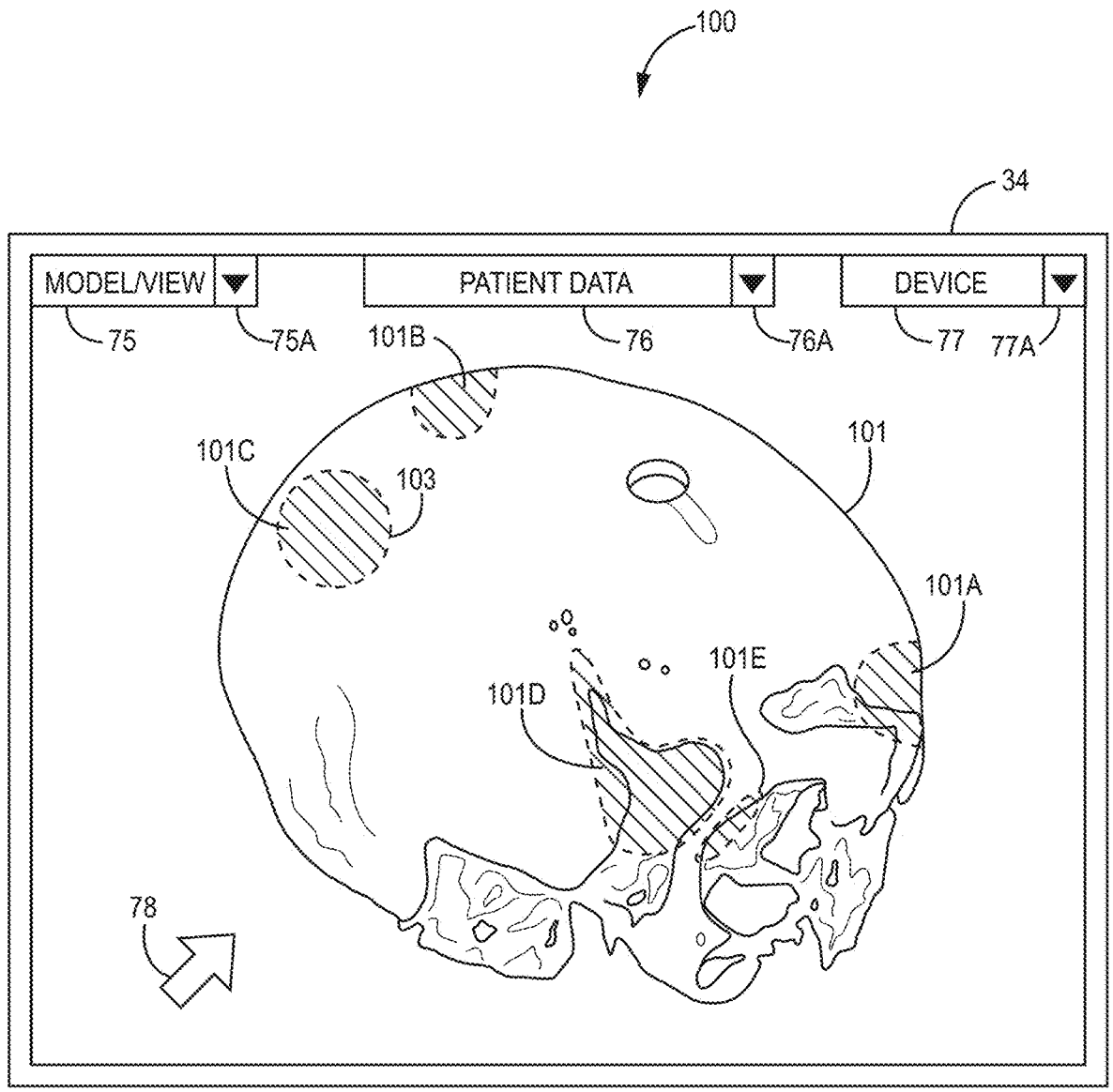
FIG. 7 illustrates an example three-dimensional image generated and displayed in accordance with the various techniques described in this disclosure.

FIG. 7 illustrates a three-dimensional image 100 generated and displayed in accordance with the techniques described in this disclosure. As shown in FIG. 7, a three-dimensional image of a skull 101 of a patient is rendered and displayed on display device 34. The three-dimensional image of skull 101 may be generated using any of the techniques and may be configured to provide and/or perform any of the features and functions associated with the image of skull model 71 as illustrated and described above with respect to FIG. 4 and with respect to skull model 91 as illustrated and described with respect to FIG. 6. The graphical display of image 100 as illustrated in FIG. 7 may include the model/view data field 75, the patient data field 76, and/or the device data field 77 as described above with respect to FIG. 4, and may provide any combination of and/or all of the features and functions described above as ascribed to data fields 75, 76, and 77, and the associated pull-down buttons.

As shown in FIG. 7, the rendering of the image of skull 101 includes the addition of image annotations defining areas 101A, 101B, 101C, 101D, and 101E, wherein each area is superimposed on the image of the skull 101, and encloses or partially encloses an area on the exterior surface of the skull 101. In various examples, the areas enclosed or partially enclosed by each of areas 101A-101E may designate areas of the skull 101 that meet particular criteria, which may be based on one or more evaluation criteria. For example, areas 101A-101E may represent areas of the skull modeled as skull model 101 that may have to be avoided when considering areas where an IMD may be implanted or affixed to the skull associated with the image of skull model 101. For example, one or more of areas 101A, 101B, 101C, 101D, and 101E may need to be in contact with a fixation device, such as frame attachment, that may need to be in place and/or in contact with the skull during at least some portion or all of an implantation or fixation procedure, and thus may not be otherwise available or accessible during the implantation procedure.

These areas meeting the defined evaluation parameter or evaluation parameters for avoidance areas may be indicated in image 100 in some examples using a color, such as an orange coloration, of the area that is determined to meet the predefined evaluation parameter or evaluation parameters. In various examples, the choice of color is a color that may be different from a color or colors used in other images, such as image 90 illustrating areas 92A-92C in FIG. 6, that are intended to designate other types of areas, such as possible implantation sites, based on a different set of evaluation parameter used to determine areas of the image annotations illustrated by areas 101A-101E in FIG. 7. In various examples, one or more of the areas enclosed or partially enclosed by areas 101A-101E may include a boundary line, such as boundary line 103 illustratively shown as encircling the area 101C, that may be used in addition to or instead of the color described above to indicate the portions of the skull that meet the predefined parameter(s).

In various examples, the predefined evaluation parameters may be adjusted, for example by changing the evaluation parameter or the evaluation parameters used to determine the areas of the skull in the image of skull model 101 should be included in areas 101A-101E in image 100. For example, the areas rendered in image 100 as one or more of areas 101A-101E may be associated with a particular device, such as a fixture, stereotactic frame, or fiducial marker, that may be defined as being used in a proposed implantation procedure, and thus defines, as an evaluation parameter, various areas of the skull that must be otherwise avoided or may be inaccessible during part or all of an implantation procedure using that particular fixture. If a user provides inputs to the system that indicate a different fixture and/or implantation process is to be viewed with respect to image 100, the system providing image 100 may be configured to re-render image 100 to indicate one or more newly defined areas that may need to be avoided or may be inaccessible during an implantation procedure based on the revised evaluation parameter(s) that may include use of the different fixture.

Using this feature, the system provides a user with the ability to better model various factors that may impact an implantation procedure, such as how different fixtures, frames, or fiducials may affect access to various portions of the skull during an implantation procedure, and to also compare various scenarios based on different fixtures, to help optimize the implantation and the implantation process for the patient under consideration.

In addition, the areas 101A-101E may also be rendered as selectable areas within image 100, and may be selected, for example using cursor 78, in a manner similar to that described above with respect to the selectable portions of image 70 and FIG. 4, (e.g., such as device 72 and dashed box 73). Referring again to FIG. 7, in some examples when one or more of areas 101A-101E is selected, image 100 may display additional information, such as information related to the device and/or the reason(s) the area or areas is/are designated as an area to avoid. In some examples, the display of image 100 may be configured so that when one or more of areas 101A-101E is selected, a user may provide inputs to the system providing image 100 that modify which evaluation parameter or evaluation parameters that are being used, and/or to modify the criteria values used to evaluate the evaluation parameter(s) defining the areas 101A-101E. Based on these inputs, the system providing image 100 may be configured to re-render image 100 and so that areas 101A-101E that may appear on skull model 101 are indicative of areas of the skull model that may need to be avoided based on the revised evaluation parameter(s) and/or the revised criteria used to evaluate the evaluation parameters with respect to areas to avoid as illustrated by image 100.

In addition, in some examples the image 100 rendered to illustrate the avoidance areas may be superimposed over another image generated by the system, such as image 90 as illustrated and described with respect to FIG. 6. By superposing image 100 over image 90, an image of a patient skull may be rendered that indicates both areas favorable for an implantation and areas that may need to be avoided during an implantation procedure, and provides an image of the overlap that may occur between any of these different types of areas.

The ability to superimpose one image over another, whether the superimposed images may include one or more areas designated for different purposes and/or based on different predefined evaluation parameters, may provide a useful tool for use in not only determining whether an implantation of a medical device may be possible, but also with respect to illustrating various aspects and evaluation parameters related to the implantation procedure itself.

Figure 8:
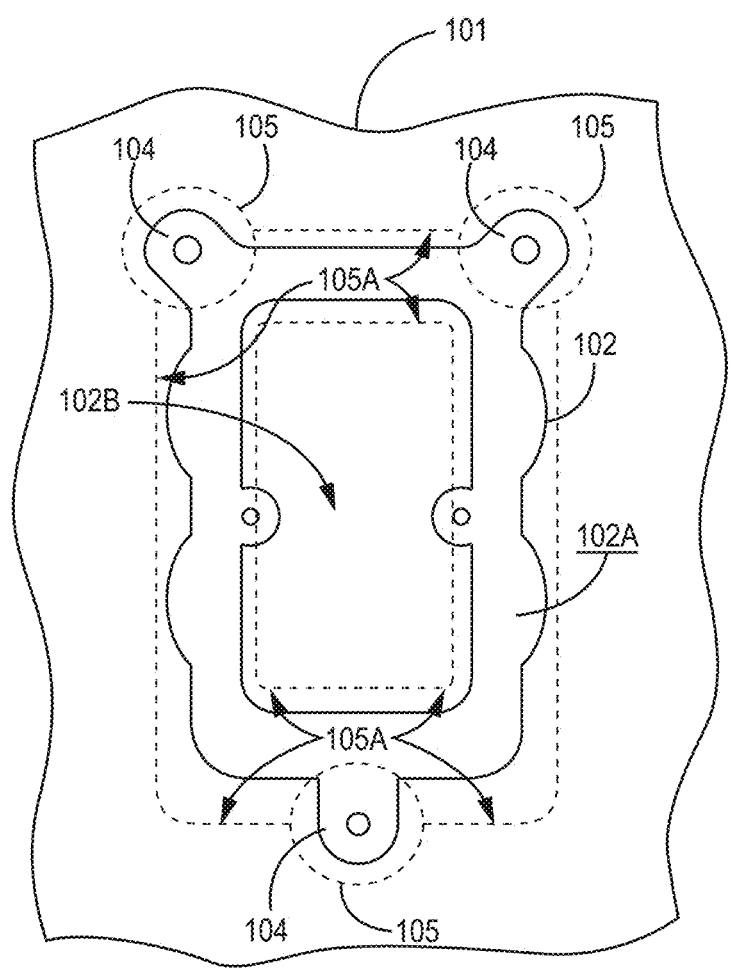
FIG. 8 illustrates an example fixture that may be modeled for use in planning an implantation for a patient in accordance with the various techniques described in this disclosure.

FIG. 8 illustrates an example fixture 102 that may be modeled for use in planning an implantation for a patient in accordance with the techniques described in this disclosure. As shown in FIG. 8, fixture 102 is formed of a framework the encircles an opening 102B through the fixture, and includes a plurality of tabs 104 extending from the sides and/or corners of the framework. Tabs 104 each includes a through hole that is configured to allow a fastener, such as a bone screw, to extend through the through hole to secure the fixture 102 to a position and affixed to a portion of the exterior surface of the skull 101 of a patient. When positioned and affixed to the skull of the patient, opening 102B provides access to an area of skull 101 through opening 102B, while allowing fixture 102 to provide support for other devices, such as cutting tools, that may be used during the implantation process. For example, a top surface 102A of fixture 102 may provide a flat surface for supporting a cutting tool, such as a router, that extends through opening 102B and is placed in contact with the skull in order to cut the skull to form a recess for an implantable medical device, while controlling the cutting tool depth and/or directional access with respect to the skull.

In various examples, fixture 102 may be elevated above the exterior surface of the skull 101 and supported by legs or extensions (not visible in the view provided in FIG. 8), extending below fixture 102, for example in the areas where tabs 104 are formed. In other examples, fixture 102 may be substantial flat and designed to contact the exterior surface of the skull in the areas of fixture formed by a flat or curved surface opposite flat surface 102A of the fixture. Fixture 102 may be an example of the "devices," such as devices 22 as illustrated and described with respect to FIG. 1, for which data, for example dimensional data, is known and is stored within the image rendering system. The system may be configured to allow a user to select fixture 102 for example using device data field 77 (described for example with respect to FIG. 4), as a device that is under consideration for use in an implantation procedure, and to model aspects of the device with respect to graphical images rendered by the system.

For example, as shown in FIG. 8 the circles representing the areas enclosed by dashed lines 105 may be associated with the data for fixture 102. When fixture 102 is selected for using in modeling an implantation procedure, the dimensioning and spacing of circles represented by dashed lines 105 may be provided as the "orange" areas such as areas 101A-101E (illustrated and described with respect to FIG. 7) that are designated as "keep out" areas that need be allocated for the placement of the fixture 102, at least during some phase or phases of the implantation process.

Having the information depicted by the dashed lines 105, and for example being able to manipulate the proposed locations of the fixture 102 in a rendered image of the skull of a patient that provides the indications provided by dashed line 105 may allow a system user to determine compatibility of use of fixture 102, or some other fixture, with various proposed implantation locations, and/or various combinations of provided medical devices for potential implantation with respect to the patient.

In another example of information that may be provided by the system, the areas of skull 101 that are enclosed between dashed line 105A, which may or may not be rendered to include the areas encloses within the dashed lines 105, may also be provided as part of an image rendered by the system as part of a planning process for a proposed implantation procedure. These additional areas indicated by the areas between dashed lines 105 may indicate areas of the skull 101 that may be blocked to direct access when the fixture 102 is in place on the exterior surface of the skull 101. For example, being able to superimpose a graphical image of fixture 102 onto a graphical image of a skull model and to have the indications provided by circles 105 superimposed onto an image of a skull that indicates skull thicknesses may help determine whether the proposed location of fixture 102 would include skull thicknesses adequate to support fasteners used to mount fixture 102 at the proposed location of the skull. This information, and the ability to manipulate the position of the fixture in the rendered image to illustrate the impact of these non-accessible areas based on different proposed positioning of fixture 102, may allow a user to better plan for the placement and/or rule out particular placements of the fixture 102 as part of the implantation planning procedure before the actual implantation process is initiated.

Figure 9:
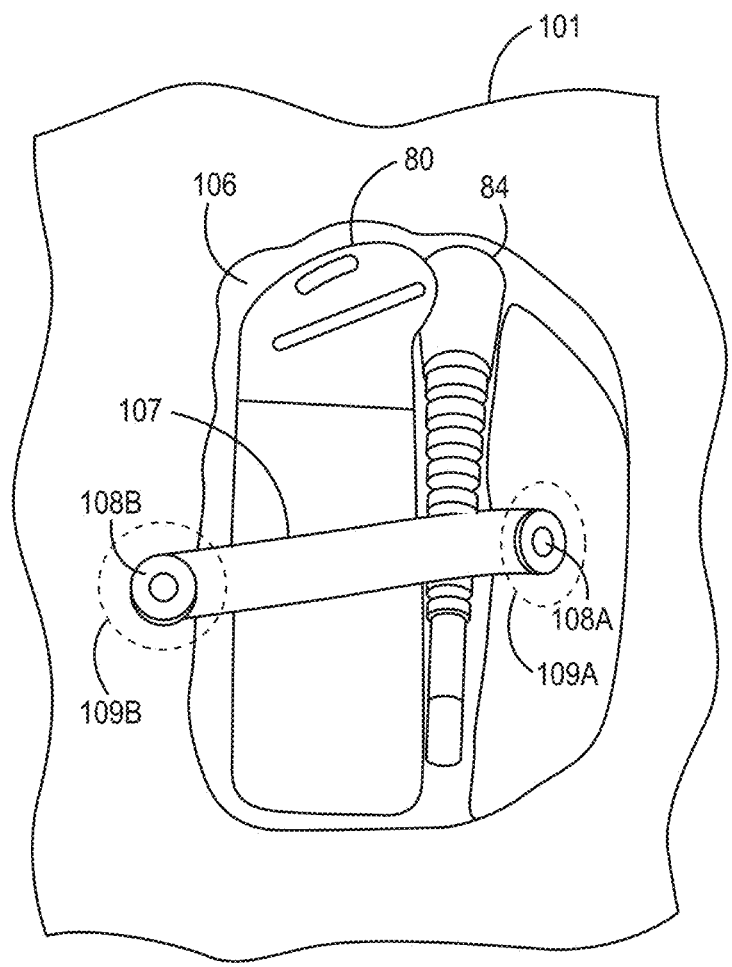
FIG. 9 illustrates an image of an example medical device fastened to a skull that may be modeled for use in planning an implantation in accordance with the various techniques described in this disclosure.

FIG. 9 illustrates an image of an example medical device 80 fastened to a skull 101 that may be modeled for use in planning an implantation in accordance with the various techniques described in this disclosure. As shown in FIG. 9, the image shows medical device 80 including an adaptor 84 positioned at least partially within a recess area 106 formed in the skull 101 of a patient. In some examples, a "partially"

recessed device includes an implantation wherein at least some portion of the medical device is located within the recess area below an exterior surface portion of the skull, and some portion of the medical device extends from the recess above the exterior surface portion of the skull. A medical device that is "wholly" implanted in a recess in the skull does not necessarily mean that the medical device is completely surrounded on all sides of the medical device by the skull. In some examples, a medical device may be considered "wholly" implanted within the recess if no portion of the medical device extends above the exterior surface of the skull, even if the recess and/or the medical device are open to the area outside the exterior surface of the skull.

Adaptor 84 may form a connection between a header of the medical device 80 and at least one stimulation lead (not specifically shown in FIG. 9). Adaptor 84 may be included for a variety of purposes, including allowing for adjustments for differences in the number or spacing of stimulating electrodes vs the device connector of the medical device 80, allowing a wider variety of models of lead to be supported, including the addition of the cranial mount device to historical lead systems already implanted. Adaptor 84 may also provide protection to the proximal end of the stimulation lead by preventing any damage during the implant surgery, or any future revision or replacement procedure involving the medical device 80 and/or a stimulation lead coupled to the medical device 80. Adaptor 84 may also aid in controlling the direction and angle of exit of electrical conductors from the medical device 80, including provisions for strain or stress relief and/or features for helping the stimulation lead to exit the bone trough created for the medical device without sharp bends or other mechanical challenges.

A strap 107 extends across the outward facing surface of the medical device 80 and across adaptor 84, and extends across the recess 106. Strap 107 is fastened at one end of the strap to a portion of skull 101 outside the areas of recess 106 by a first fastener 108A, and is fastened at the opposite end of the strap to a portion of the skull 101 outside the area of recess 106 and on an opposite side of the recess 106 by a second fastener 108B. Strap 107 and fasteners 108A, 108B provide a mechanism to physically secure medical device 80 within recess 106. As shown in FIG. 9, a circle enclosed by dashed area 109A surrounds the areas of skull 101 were fastener 108A is located, and a circle enclosed by dashed area 109B surrounds the area of skull 101 were fastener 108B is located. In various examples, data associated with device 80 and/or strap 107 and/or fasteners 108A, 108B may be included in the image rendering system, and used to generated information associated with the circles depicted by dashed lines 109A, 109B. For example, the diameter and spacing of circles illustrated by dashed lines 109A, 109B may be generated as part of a rendered image of a skull, and utilized as part of the planning of an implantation process.

For example, of a particular type of fasteners for fasteners 108A, 108B may require a minimum skull thickness in the areas indicated by dashed lines 109A, 109B respectively. In addition, there may be a minimum spacing requirement between the area ideated by circles 109A, 109B, and the edges of the recess 106. By modeling the proposed placement of medical device 80 within a rendered image the skull of a patient, the areas that would be associated with the strap and fasteners can be indicated on the rendered image of the skull model, and the system can also determine whether the area of the skull that could be configured for fixation using fasteners 108A, 108B can provide the required skull thickness in the areas indicated for each of the fasteners is adequate. A color indication, such as green or red coloration, could be used to fill in circles 109A, 109B, the color or colors providing an indication of whether the proposed location of the strap and the associated fasteners complies with the requirements, such as skull thickness and/or spacing from the edges of a recess, for use of the proposed type of fasteners.

Based upon this information, a user may for example choose a different location for the strap, different lengths or shapes of strap, or may consider using one or more different fasteners for use in a proposed implantation procedure, that based on skull thickness and/or location of the fasteners relative to the edges of the recess, would meet the requirements for using the particular type of fasteners 108 in the location.

Figure 10:
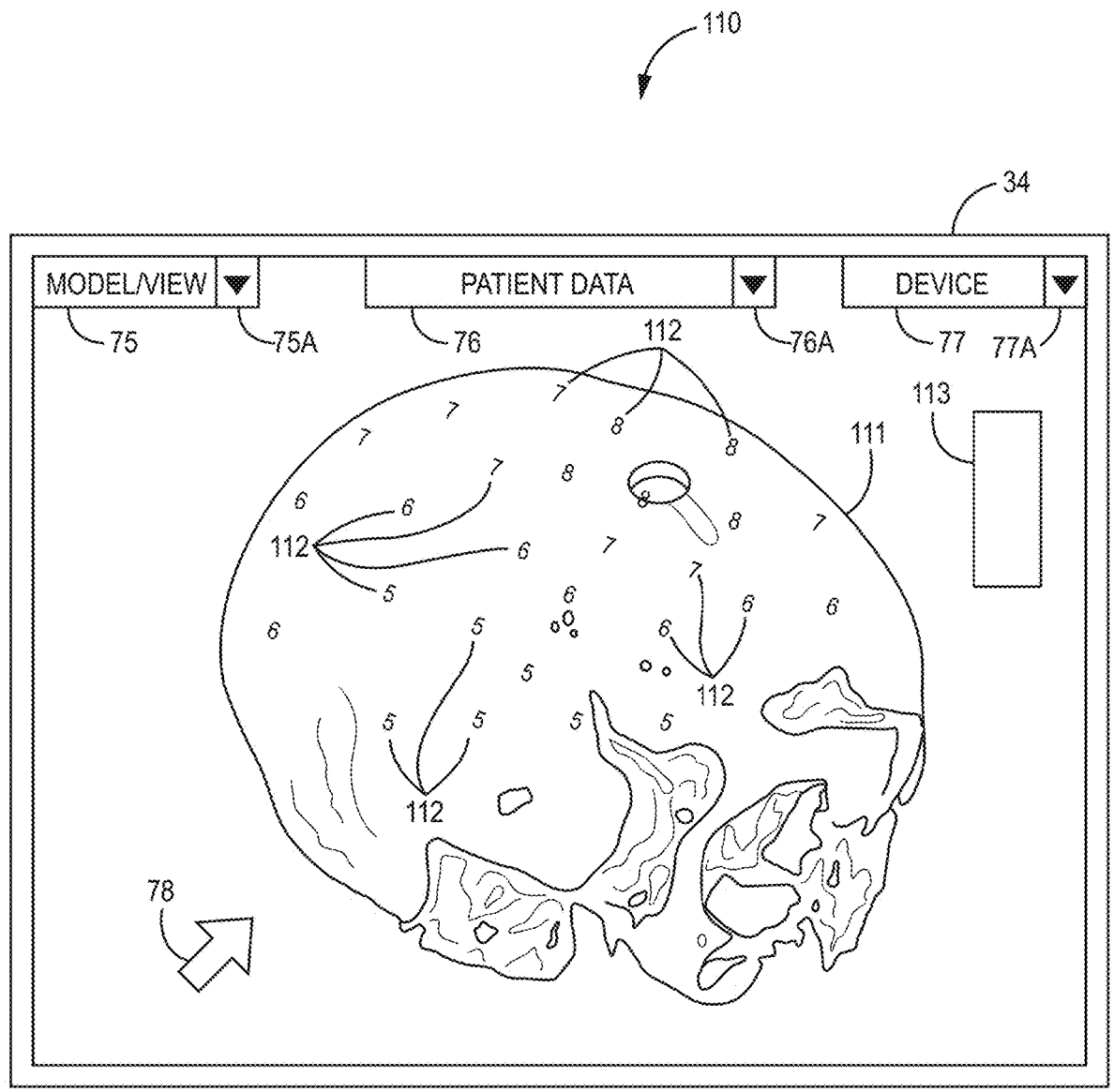
FIG. 10 illustrates an example three-dimensional image generated and displayed in accordance with the various techniques described in this disclosure.

FIG. 10 illustrates an example three-dimensional image 110 generated and displayed in accordance with the various techniques described in this disclosure. As shown in FIG. 10, a three-dimensional image of a skull model 111 of a patient is rendered and displayed on display device 34. The three-dimensional image of skull model 111 may be generated using any of the techniques and may be configured to provide and/or perform any of the features and functions associated with respect to the image of skull model 71 as illustrated and described above with respect to FIG. 4, with respect to the image of skull model 91 as illustrated and described above with respect to FIG. 6, and with respect to skull model 101 as illustrated and described above with respect to FIG. 7. The graphical display of image 110 as illustrated in FIG. 10 may include the model/view data field 75, the patient data field 76, and/or the device data field 77 as described above with respect to FIG. 4, and may provide any combination and/or all of the features and functions described above as ascribed to these fields, and the associated pull-down buttons.

As shown in FIG. 10, the rendering of the image of skull model 111 includes the addition of a plurality of image annotations 112, illustrated as single digit numbers distributed across the exterior surface of the skull model 111. The value associated with the single digit number in some examples may be an overall value associated with some parameter selected for illustration in the graphical image of skull model 111. For example, the numbers may be representative of a parameter associated with skull thickness around the skull where the number appears in the image. As show in FIG. 10, some of the numbers have a value of "8," others having a value of "7," of "6" or of "5". These values may be associated with an actual value of the thickness of the skull in millimeters in the portion of the skull where the number appears in the graphical image of the skull model 111. In some examples, the value of these numbers may be a value that is relative in magnitude to each other, wherein a higher value number represents a portion of the skull that is thicker by some amount relative to the areas of the skull where numbers with lower value(s) are positioned in the image of the skull model.

These indications of values related to skull thickness may be used by a user, for example by a surgeon, to evaluate various portions of the skull being modeled by the graphical image of skull model 111 for various purposes, including evaluation of possible locations for implantation of an IMD, evaluation of locations that may accept some decree of recess formed into the skull for the implantation of the IMD, evaluation of areas that may be better suited for burr holes to be formed through the skull to provide access to the target structure and/or tissues within the skull, and for evaluation with respect to portions of the skull that may be more or less suitable for attachment of one or more devices, such as fixture, that may be required to be in contact with, and in some examples fastened to the skull during some portion of the implantation procedure.

The use of the numbering as illustrated in FIG. 10 is intended to be illustrative and non-limiting with respect to the type of symbols that may be used to depict information associated with the skull model 111. Other symbols besides numbers, such as letters, or graphical symbols such as arrows or geometrical shapes such as squares, triangles, and circles may be used in place of the numbers shown in FIG. 10 to indicate various parameters associated with the skull being modeled by skull model 111. In addition, other evaluation parameters besides skull thickness, such as skull contour/flatness, scalp thickness, presence or absence of hair, and rankings related to cosmetic and/or interference with other devices such as glasses or hearing aids worn by the patient may also be ranked according to various criteria, and the rankings provided as numbers or other graphical symbols superimposed on skull model 111 in a manner similar to that illustrated by image 110 in FIG. 10.

In various examples, a combination of numbers and/or letters and/or graphical symbols may be provided in a same image of skull model 111 to deceit different parameters. For example, numbers may be illustrated to depict skull thicknesses at different portion of the skull being modeled, wherein letters such as "A," "B" and "C" maybe used to indicate a ranking of patient preferences for possible locations of implantation of an IMD from a cosmetic standpoint. In some examples, image 110 includes and illustration of a key 113 that explains and/or illustrates the specifics of the image annotation 112 being illustrated within skull model 111, for example illustrating how the numbers, letters, or other graphical symbols relate to parameter(s) associated with the skull model.

In some examples, the various parameters being depicted by image annotations 112 may be weighted relative to one another. For example, indication of a parameter associated with skull thickness may be given a heavier weighting than for example the cosmetic ranking values indicated by the patient. These different weightings for the various parameters may be combined, for example in some form of a weighted average, to determine the values (numerical value) assigned to each of the numbers illustrated as image annotations 112 shown in image 110. The numerical value that is displayed as image annotations 112 may be an indication a 'goodness' or 'suitability' index for example when comparing different possible locations for implanting an IMD based on the weighted factors combined to determine the values for each of the numbers displayed at the various portion of the skull being modeled as skull model 111.

Figure 11:
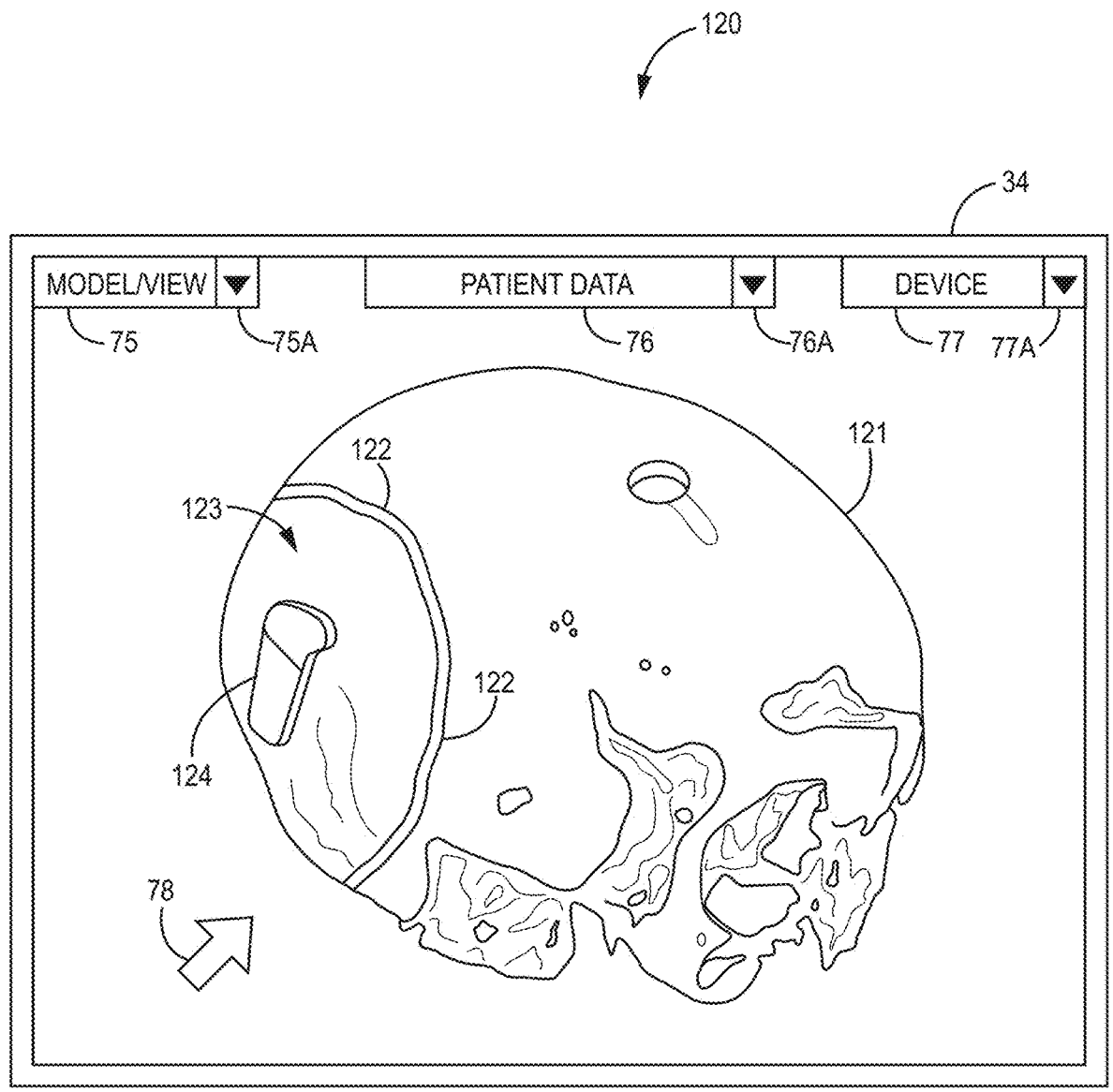
FIG. 11 illustrates an example three-dimensional image generated and displayed in accordance with the various techniques described in this disclosure.

FIG. 11 illustrates an example three-dimensional image 120 generated and displayed in accordance with the various techniques described in this disclosure. As shown in FIG. 11 a three-dimensional image of a skull 121 of a patient is rendered and displayed on display device 34. The three-dimensional image of skull model 121 may be generated using any of the techniques and may be configured to provide and/or perform any of the features and functions associated with the image of skull model 71 as illustrated and described above with respect to FIG. 4, with respect to skull model 91 as illustrated and described with respect to FIG. 6, with respect to skull model 101 as illustrated and described with respect to FIG. 7, and with respect to skull model 111 illustrated and described with respect to FIG. 10. The graphical display provided as part of image 120 as illustrated in FIG. 11 may include the model/view data field 75, the patient data field 76, and the device field 77 as described above with respect to FIG. 4, and may provide any combination and/or all of the features and functions described above as ascribed to data fields 75, 76, and 77, and the associated pull-down buttons.

As shown in FIG. 11, the rendering of the image of skull 121 includes the addition of an implanted medical device 124. The rendering of the device 124 positioned on the exterior surface of the image of skull model 121 may be based on an existing implantation for the patient, or based on a proposed implantation for the patient. In addition to the rendering of the device 124, image 120 further includes a rendering of a boundary line 122 that partially encloses an area 123 surrounding the device 124. In various examples, the area 123 relates to an area defined by one or more evaluation parameters associated with device 124. For example, devices 124 may have certain requirements, such as a minimum separation distance, that should be maintained between device 124 and another device, such as a second medical device. The minimum separation distance may be due to issues and parameters associated with recharging, telemetry, sensing signal quality, or other considerations that may affect the quality of the operation of the device 124, and/or patient comfort. In some examples, the area 123 may be considered a "keep-out" zone wherein based on and implantation of device 124 at the location as rendered in image 120, the area 123 and boundary 122 provides an indication of areas or regions of the skull were other, for example a second medical device, should not be implanted.

Thus, image 120 may provide a graphical illustration of an evaluation parameter, e.g., a required minimum separation that must be maintained between device 124 and other IMDs or devices when these devices and device 124 are implanted together on the skull of a patient. In various examples, the criteria used to evaluate this evaluation parameter associated with the skull model 121 and device 124 is a threshold minimum distance. Using the predefined values as a threshold minimum distance, the system providing image 120 may be configured to determine the area around device 124 that is within a distance less than the threshold minimum distance, and to render an image of a boundary line 122 that encloses or partially encloses the area 123.

In various examples, boundary line 122 and/or area 123 may be graphically illustrated using various graphical indications, for example a solid line may be rendered on the image of skull model 121 to indicate the boundary line 122, and a color, such as red, may be used to render the area enclosed or partially enclosed by boundary line 122 that indicates the "keep out" zone associated with the positioning of device 124 at the location graphically depicted in skull model 121.

In various examples, the graphical image of device 124 is selectable in image 120, and when selected, may be repositioned to different locations relative to the skull being modeled by skull model 121. The system providing image 120 may configured to re-render and to display a re-rendered image illustrating any adjustments to the boundary line 122 and/or to area 123 in response to a change in the location of device 124. In various examples, the system providing image 120 is configured to receive inputs to the system, for example for a user, that adjust the value being used at the minimum separation threshold. The system providing image 120 may be configured to re-render and to display a re-rendered image illustrating any adjustments to the boundary line 122 and/or to area 123 in response to a change threshold value assigned to the minimum separation distance relative to device 124. In some examples, the system providing image 120 may allow for replacement of device 124, with a different device, such as a different IMD, based on inputs to the system for example provided by a user. The system providing image 120 may be configured to re-render and to display a re-rendered image illustrating any adjustments to the boundary line 122 and/or to area 123 in response to a change in the device that was selected based on user inputs received at the system. These features may allow a user, such as a surgeon, to evaluate various scenarios with respect to the positioning of a device, such as device 124, and the positioning of other devices contemplated for use or based on existing devices when planning an implantation procedure.

In other examples, where one or more devices may be considered to be compatible with one and other, and for example where it may be desirable to recharge, say inductively recharging multiple devices with a common recharging devices and/or a same recharging session, area 123 as indicated in the rendered image 120 may indicate a maximum distance of separation that may occur between device 124 and a second implanted medical device that would still allow recharging of both devices by a common recharging device and/or a common recharge process. Based on the boundary line 122 and/or the area depicted in image 120, a user, such as a surgeon, may determine the maximum separation, and may evaluate areas within area 123, that may be favorable for implantation of a second device based on the proposed location for the implantation of device 124.

In various examples, image 120 may be superimposed over any of the images described throughout this disclosure that depict additional information related to skull size, skull thickness, skull shape (e.g., skull curvature/flatness), scalp thickness, and/or images related to blood vessels and/or nerves within the scalp of a patient and/or related to lead routings. The feature allowing the superimposing of image 120 over other images may allow the evaluation parameters related to minimum separation distance and or to maximum separation distance related to multiple device implantation to be evaluated in view of other evaluation parameters in a more easily understandable and/or more rapid fashion.

Figure 12:
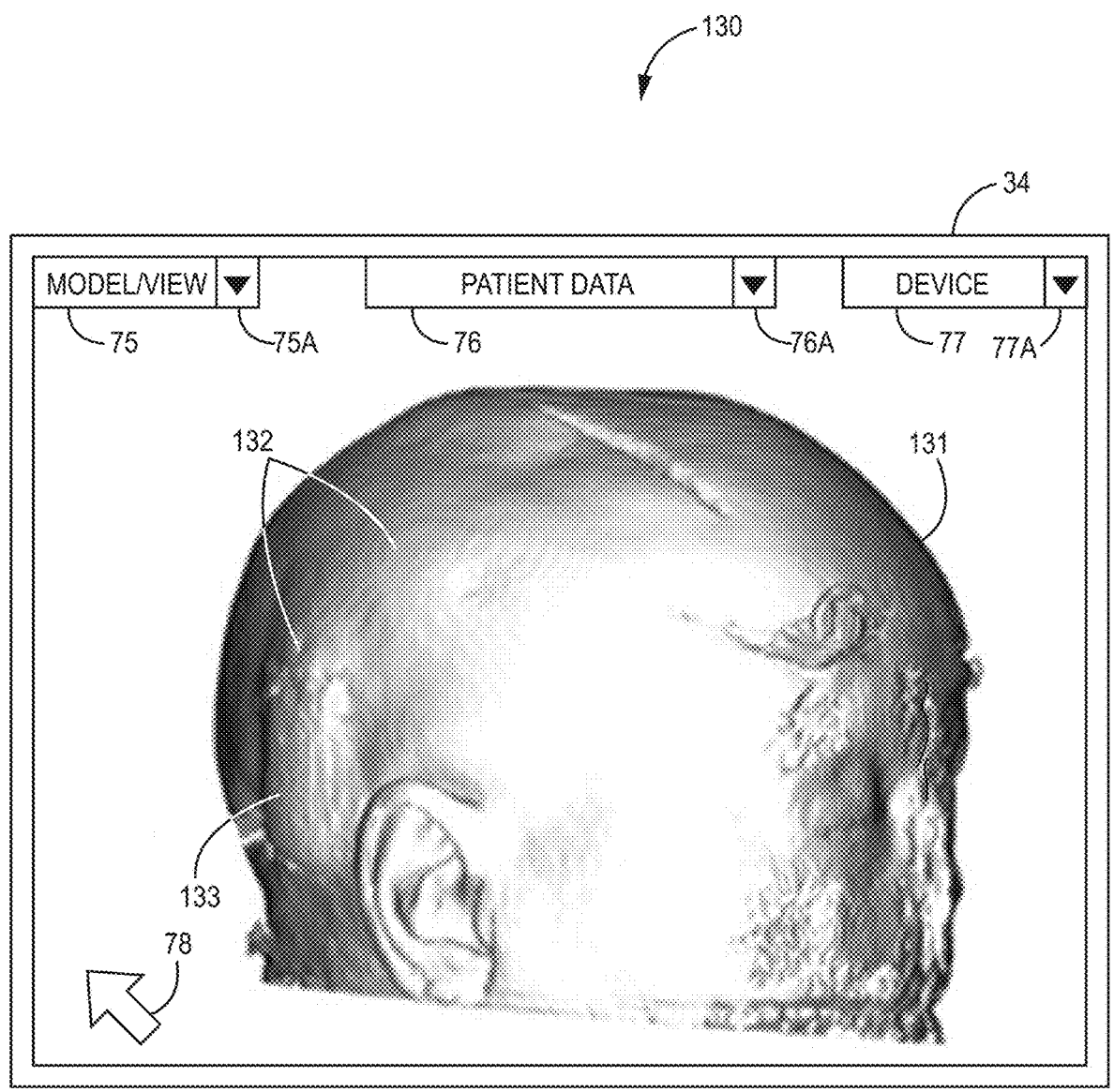
FIG. 12 illustrates an example three-dimensional image generated and displayed in accordance with the various techniques described in this disclosure.

FIG. 12 illustrates an example three-dimensional image 130 generated and displayed in accordance with the various techniques described in this disclosure. The three-dimensional image of skull model 121 may be generated using any of the techniques and may be configured to provide and/or perform any of the features and functions associated with the image of skull model 71 as illustrated and described above with respect to FIG. 4, with respect to skull model 91 as illustrated and described with respect to FIG. 6, with respect to skull model 101 as illustrated and described with respect to FIG. 7, with respect to skull model 111 illustrated and described with respect to FIG. 10, and with respect to skull model 121 illustrated and described with respect to FIG. 11. The graphical display provided as part of image 120 as illustrated in FIG. 11 may include the model/view data field 75, the patient data field 76, and the device field 77 as described above with respect to FIG. 4, and may provide any combination and/or all of the features and functions described above as ascribed to data fields 75, 76, and 77, and the associated pull-down buttons.

As shown in FIG. 12, a three-dimensional image of the head portion of a patient 131 including an image of an IMD implanted relative to the patient is displayed as part of image 130. In image 130, the image of the scalp 132 is simulated in place over the IMD 133, and is rendered and displayed on display device 34. In some examples, the image of IMD 133 may be manipulated with respect to the location of the device relative to the head portion of the image of the patient 131, and the image of the scalp 132 re-rendered in respond to the relocation of the IMD to illustrate the cosmetic impact on the scalp that may occur as a result of the relocation of the IMD.

In some examples, the image of the IMD 133 may be manipulated to show the IMD as implanted with a pre-defined amount to recess relative to the location of the IMD and the exterior surface of the skull of the patient. The image of the scalp 132 may be re-rendered in respond to the variations in the amount of recess of the IMD relative to the surface of the skull of the patient to illustrate the cosmetic impact on the scalp that may occur as a result the use of various amounts of recess with respect to the skull of the patient and the IMD. In various examples, other devices such as glasses or a hearing aid device (not shown in FIG. 12) may be selected, for example using device field 77, and rendered onto the image provided as image 130 to help illustrate any interactions, and/or clearance issues that may occur between these added devices and the proposed location of the implantation of IMD 133.

Figure 13:
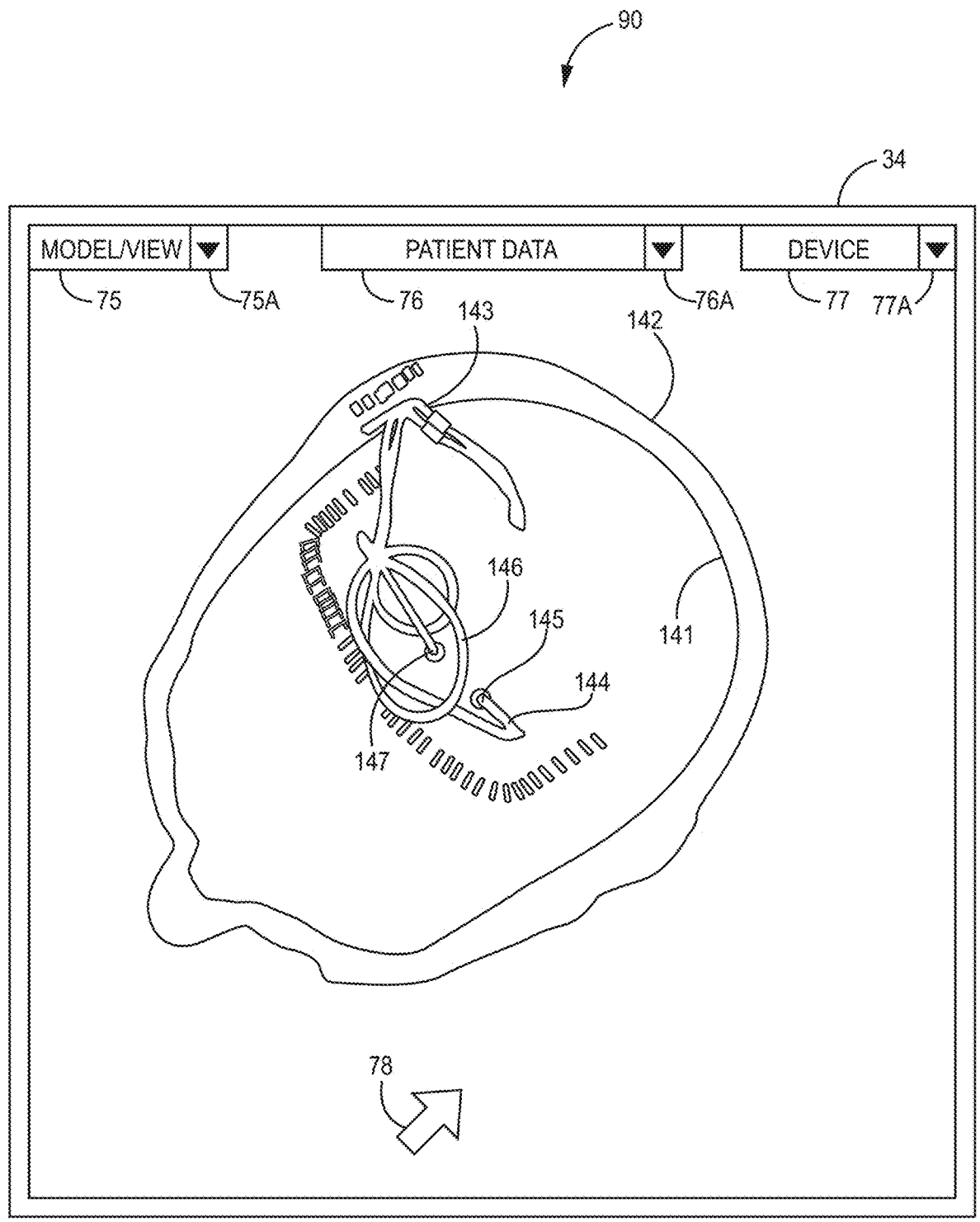
FIG. 13 illustrates a plan view of an example image generated and displayed in accordance with the various techniques described in this disclosure.

FIG. 13 illustrates a plan view of an example image 140 generated and displayed in accordance with the various techniques described in this disclosure. As shown in FIG. 13, plan view of a skull 141 of a patient is rendered and displayed on display device 34. The image 140 may include additional graphical depictions of the scalp 142 of the patient. The three-dimensional image 140 may be generated using any of the techniques and may be configured to provide and/or perform any of the features and functions associated with the image of skull model 71 as illustrated and described above with respect to FIG. 4, with respect to skull model 91 as illustrated and described with respect to FIG. 6, with respect to skull model 101 as illustrated and described with respect to FIG. 7, and with respect to skull model 111 illustrated and described with respect to FIG. 10, with the skull model 121 illustrated and described with respect to FIG. 11, and with respect to simulation image 131 illustrated and described with respect to FIG. 12.

The graphical display of image 140 as illustrated in FIG. 13 may include the model/view data field 75, the patient data field 76, and/or the device data field 77 as described above with respect to FIG. 4, and may provide any combination and/or all of the features and functions described above as ascribed to these fields, and the associated pull-down buttons.

As shown in FIG. 13, an IMD 143 is illustrated as located on a right-hand side of the image of skull 41. A first electrical lead 144, is routed from the implantable medical device 143 to a burr hole 145 located in the top of the image of the skull 141. A second electrical lead 146 is routed from the IMD 143 to a second burr hole located in the top of the image of skull 141 and in an area of the skull adjacent to the first burr hole. Each of lead 144, 146 may comprise a portion of the lead that extends through the respective burr holes 145, 147, to target tissue of the patient's brain located within the skull of the patient. The leads may include one or more electrodes that are electrically coupled to circuitry of the IMD 143 by electrical conductors provided with the leads 144, 146. When implantation of IMD 143 and leads 144, 146 has been completed, the IMD 143 may be configured to provide therapy, such as electrical stimulation therapy, and/or to monitor signals, such as a neurological signal of the patient through the electrodes coupled to the IMD through leads 144, 146.

As part of planning the implantation process that includes IMD 143 and lead 144, 146, various factors, such as the final implantation site of the IMD 143, the orientation of the leads 144, 146 leaving the IMD 143 once IMD 143 is implanted, the routing and looping requirements associated with the leads relative to the positioning of IMD 143 and the location of one or more the burr holes, may all need to be considered as part of the planning process of the IMD 143 and lead 144, 146. The image 140 may be generated and displayed by a system, such as system 10 illustrated and described with respect to FIG. 1, to allow a user to model and manipulate various parameters associated with the proposed implantation of IMD 143 and leads 144, 146 with respect to all these factors in order to study and compare various scenarios, and to plan for the most optimal process for the implantation of IMD 143 and the routing of leads 144, 146.

For example, the features and functions associated with the rendering of image 140 may be used to determine, and to render an image depicting the proposed location for IMD 143 as part of image 140. Once a proposed location of the IMD 143 is determined, various other parameters associated with the implantation procedure may be rendered and illustrated as part of image 140. For example, data related to the lengths of leads 144, and 146 may be provided to the system rendering image 140, and the allow a user to manipulate, for example using cursor 78, the proposed routings of leads 144 and 46 based the known location and orientation of IMD 143 and data associated with the location of burr holes 145, 146. The graphical display of image 140 may allow a user to select a point along the image of a lead 144, 146, and to drag that portion of the lead within the image to various positions within the image representative of different location relative to the skull, so that the image of the routing of the lead, may be manipulated.

By being able to graphically manipulate the routing the lead, a user can experiment with various lead routings, and for example be provided with data related to whether or not the length of the leads that are proposed for use with the implantation procedure are long enough to meet all the routing requirements, including any required looping for the leads based on the proposed routings. In some examples, a proposed routing of a lead between IMD 143 and burr holes 145, 147 may be proposed by manipulation of the image of the leads provided in image 140, and the system may then render an information, for example a text information provided in some portion of the image 140, of a minimum lead length the would be required to provide the proposed lead routing based on the location of IMD 143 and the burr holes 145, 147 provided in image 140. This feature may be integrated into the rendering of image 140 to show a user how different proposed lead routing may be affected by or have an impact on the blood vessels and/or nerve location of these tissues within the scalp 142 of the patient associated with the skull 141 and scalp 142 as provided in image 140. It may also show the lead routings relative to a proposed incision location, which may be of interest in ensuring that leads are not damaged if or when the incision must be opened for a replacement device in the future.

Figure 14:
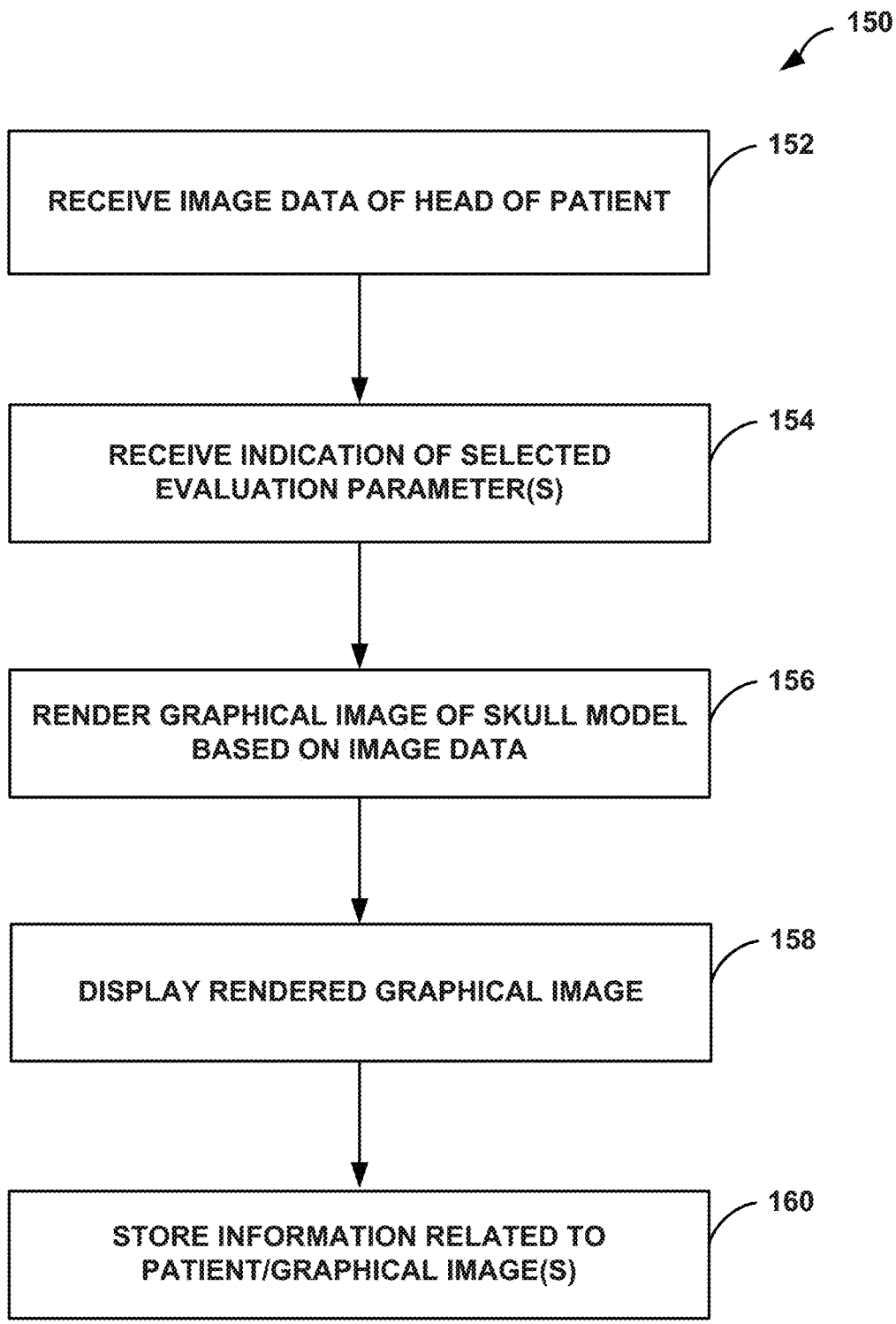
FIG. 14 is a flow diagram illustrating a method in accordance with the various techniques described in this disclosure.

FIG. 14 is a flow diagram illustrating a method according to the various examples described in this disclosure. Although method 150 is described as being performed by workstation 32 as illustrated and described with respect to FIG. 1 and FIG. 2, method 150 is not limited to being performed by any particular device or devices, and may be performed by any device or devices configured to perform the functions of method 150, including devices and systems as otherwise described herein.

According to method 150, processing circuitry, such as processing circuitry 2 included within workstation 32, receives image data of a head of a patient (block 152). Image data may be data generated by imaging equipment 12 as illustrated and described with respect to FIG. 1, and may include data generated by X-ray, magnetic resonance imaging, CT-scan and fluoroscopy.

Processing circuitry 2 also receives an indication of one or more selected evaluation parameters (block 154). Evaluation parameters may include parameters associated with a skull of a patient, including skull thickness, skull size, skull shape, including contour and/or flatness information associated with the skull of a patient. Evaluation parameters may also include parameters associated with the scalp of a patient, such as scalp thickness, robustness and general condition over various portions of the scalp. Evaluation parameters may also include areas defined as areas of the skull of the patient that need to be avoided or that may be inaccessible during an impanation procedure due for example to the need to have devices such as fixtures and/or frameworks in contact with the skull during the implantation procedures.

In some examples, the evaluation parameters may include a separation distance defined for an implantable medical device, wherein the separation distance defines either a minimum separation distance that should be maintained between the implantable medical device and another device to be implanted on the skull of the patient, or a maximum separation distance that should be used between the implantable medical device and another device to be implanted on the skull of the patient.

According to method 150, the processing circuitry, such as processing circuitry 2 included within workstation 32, is configured to render a graphical image comprising a skull model based on the image data (block 156). The skull model may comprise one or more image annotations superimposed onto the skull model. The image annotation may be determined based on an evaluation of the one or more evaluation parameters. The configuration of the image annotations rendered with the image of the skull model(s) may be determined based on the one or more evaluation parameters.

In some examples, the rending of the graphical image of the skull model comprises rendering a graphical image of an implantable medical device positioned on a surface of the skull model, and rendering a boundary line superimposed on the skull model indicative of an area of the surface of the skull model located within the separation distance relative to the position of the graphical image of the implantable medical device. In some examples, the separation distance comprises a minimum separation distance that defines a required minimum separation to be maintained between the implanted medical device and another implantable medical device to be implanted on the skull of the patient being modeled by the skull model. In some examples, the separation distance comprises a maximum separation distance that defines a maximum allowable separation between the implanted medical device and another implantable medical device to be implanted on the skull of the patient being modeled by the skull model.

In examples, rendering the image of the skull model may include receiving, at the processing circuitry, an input selecting the graphical image of the implantable medical device, receiving, at the processing circuitry, an input that repositions the implantable medical device at a new location relative to the skull model; and re-render, by the processing circuitry, the boundary line superimposed on the skull model based on the new location of the implantable medical device. In examples, rendering the image of the skull model may include receiving, at the processing circuitry, an input providing a new threshold value for the separation distance defined for the implantable medical device, and re-render, by the processing circuitry, the boundary line superimposed on the skull model based on the new threshold value for the separation distance. In examples, rendering the image of the skull model may include receiving, at the processing circuitry, an input indication selection of a different implantable device to replace the implantable device in the graphical image of the skull model, and re-render, by the processing circuitry, the boundary line superimposed on the skull model based on a different separation distance associated with the different implantable medical device. Re-rendering may include output for display on a display device such as display device 34, the re-rendered graphical image comprising the boundary line superimposed on the skull model based on the different separation distance associated with the different implantable medical device.

In examples, rendering the image of the skull model may include rendering a graphical image of an implantable medical device positioned on the skull model; and rendering a graphical image of one or more leads coupled between the implantable medical device and one or more graphical images of one or more burr holes located on the skull model. In some examples, the graphical image of the one or more leads may be configured to allow selection of the one or more leads in the graphical image, and to manipulate the routing of the graphical image of the lead between the implantable medical device and the graphic image of the one or more burr holes.

Method 150 may further include displaying, on a display device such as display device 34 of workstation 32, the rendered graphical image comprising the skull model (block 158). In some examples, displaying the skull image includes displaying the skull image with and the one or more image annotations superimposed onto graphical image of the skull model. In some examples, displaying the rendered graphical image may include display of a re-rendered graphical image the was re-rendered based on inputs received by the processing circuitry. Display of graphical images at display device 34 may include display of various features other than the skull models, including display of data fields, computer cursors, key menus, and/or other graphical items described throughout this disclose.

Method 150 may further include storing information related to a patient and/or the graphical images rendered and/or displayed by workstation 32 (block 160). Storing information may include storing any type of information, including data related to graphical images rendered by the workstation 32 into memory, such as database 24 illustrated and described with respect to FIG. 1 and/or such as memory 6 illustrated as described with respect to FIG. 2. The information to be stored is not limited to any particular information, and may include for example any information associated with rendered and/or displayed graphical images, including images of skull models, with or without the addition of images of IMDs, superimposed on the images of the skull models, and with or without the additional of any image annotations generated by processing circuitry 2 in association with images of the skull models.

For example, one or more skull models associated with a patient that were rendered and displayed with various image annotations superimposed on the images of the skull models may be saved in memory for later retrieval. In addition, any additional information, such as text information input into the system by a user, for example associated with the patient themselves, with one or more medical devices, and/or with respect to a proposed implantation procedure or an implantation procedure underway, and/or post implantation may be stored in memory for later retrieval. The storing of the information may include linking the stored information to a particular patient in some examples, linking the information to a particular medical device, e.g., a particular IMD in some examples, and in some examples linking the information to a combination of a patient and one or more medical devices. The stored information may be generated for example during the planning stages of a proposed implantation procedure for a patient, and then later retrieved for display and use during the actual implantation procedure, for example to aid in providing information and/or guidance that was developed during the planning procedure. Such guidance information might be used in conjunction with a navigation system, to allow a surgeon to place elements (INS, leads, incisions) accurately according to plan during the surgery. Such guidance might be used in conjunction with a projection or other augmented reality system to allow the surgeon to directly visualize the plan during the course of surgery. Finally, such guidance might be used to directly inform the motions of a robotic system configured to perform portions of the surgical procedure.

The techniques of this disclosure may be implemented in a wide variety of computing devices, medical devices, or any combination thereof. Any of the described units, modules or components may be implemented together or separately as discrete but interoperable logic devices. Depiction of different features as modules, units, circuits, or circuitry, is intended to highlight different functional aspects and does not necessarily imply that such modules, units, circuits, or circuitry must be realized by separate hardware or software components. Rather, functionality associated with one or more modules, units, circuits, or circuitry may be performed by separate hardware or software components, or integrated within common or separate hardware or software components.

The techniques described in this disclosure may be implemented, at least in part, in hardware, software, firmware, or any combination thereof. For example, various aspects of the techniques may be implemented within one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, or other devices. The terms "processor," "processing circuitry," "processing circuit," "controller" or "control module" may generally refer to any of the foregoing logic circuitry, alone or in combination with other logic circuitry, or any other equivalent circuitry, and alone or in combination with other digital or analog circuitry.

For aspects implemented in software, at least some of the functionality ascribed to the systems and devices described in this disclosure may be embodied as instructions on a computer-readable storage medium such as random-access memory (RAM), read-only memory (ROM), non-volatile random-access memory (NVRAM), electrically erasable programmable read-only memory (EEPROM), FLASH memory, magnetic media, optical media, or the like that is tangible. The computer-readable storage media may be referred to as non-transitory. A server, client computing device, or any other computing device may also contain a more portable removable memory type to enable easy data transfer or offline data analysis. The instructions may be executed to support one or more aspects of the functionality described in this disclosure.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache).

Various aspects of this disclosure have been described. These and other aspects are within the scope of the following claims.

What is claimed is:

1. A method comprising:
    receiving, at a processing circuitry, image data of a head of a patient;
    receiving, at the processing circuitry, an indication of one or more selected evaluation parameters including at least a separation distance defined between a first implantable medical device and a second implantable medical device;
    rendering, by the processing circuitry, a graphical image comprising the first implantable medical device positioned on a surface of a skull model based on the image data, the skull model comprising one or more image annotations comprising at least a boundary line superimposed onto the skull model indicative of an area of the surface of the skull model located within the separation distance relative to the position of the first implantable medical device, the image annotations determined based on an evaluation of the one or more selected evaluation parameters; and
    displaying, on a display device, the rendered graphical image comprising the first implantable medical device positioned on the surface of the skull model and the one or more image annotations.

2. The method of claim 1, wherein the separation distance comprises a minimum separation distance that defines a required minimum separation to be maintained between the first implantable medical device and the second implantable medical device to be implanted on the skull of the patient being modeled by the skull model.

3. The method of claim 1, wherein the separation distance comprises a maximum separation distance that defines a maximum allowable separation between the first implantable medical device and the second implantable medical device to be implanted on the skull of the patient being modeled by the skull model.

4. The method of claim 1, further comprising;
    receiving, at the processing circuitry, an input selecting the graphical image comprising the first implantable medical device;
    receiving, at the processing circuitry, an input that repositions the first implantable medical device at a new location relative to the skull model;
    re-rendering, by the processing circuitry, the boundary line superimposed onto the skull model based on the new location of the first implantable medical device; and
    displaying, on a display device, the re-rendered graphical image comprising the boundary line superimposed on the skull model based on the new location of the first implantable medical device.

5. The method of claim 1, further comprising;
    receiving, at the processing circuitry, an input providing the separation distance defined for the first implantable medical device;
    re-rendering, by the processing circuitry, the boundary line superimposed onto the skull model based on the separation distance; and
    displaying, on a display device, the re-rendered graphical image comprising the boundary line superimposed on the skull model based on the separation distance.

6. The method of claim 1, further comprising;
    receiving, at the processing circuitry, an input indicating a selection of a different implantable medical device to replace the first implantable medical device in the graphical image comprising the skull model;
    re-rendering, by the processing circuitry, the boundary line superimposed onto the skull model based on a different separation distance associated with the different implantable medical device; and
    displaying, on a display device, the re-rendered graphical image comprising the different implantable medical device positioned on the surface of the skull model and the boundary line superimposed on the skull model based on the different separation distance associated with the different implantable medical device.

7. The method of claim 1, wherein receiving the image data comprises receiving one or more images generated by at least one of X-ray, magnetic resonance imaging, CT-scan and fluoroscopy.

8. The method of claim 1, wherein rendering the graphical image comprising the first implantable medical device positioned on the surface of the skull model further comprises:
    rendering a graphical image of the first implantable medical device positioned on the skull model; and
    rendering a graphical image of one or more leads coupled between the graphical image of the first implantable medical device and a graphical image of one or more burr holes located on the skull model;
    wherein the graphical image of the one or more leads is configured to allow selection of the one or more leads in the graphical image, and to manipulate the routing of the graphical image of the one or more leads between the graphical image of the first implantable medical device and the graphical image of the one or more burr holes.

9. A system comprising:
    a processing circuit configured to:
        receive image data of a head of a patient;
        receive an indication of one or more selected evaluation parameters including at least a separation distance defined between a first implantable medical device and a second implantable medical device; and
        render a graphical image comprising the first implantable medical device positioned on a surface of a skull model based on the image data, the skull model comprising one or more image annotations comprising at least a boundary line superimposed onto the skull model indicative of an area of the surface of the skull model located within the separation distance relative to the position of the first implantable medical device, the image annotations determined based on an evaluation of the one or more selected evaluation parameters; and
    a display device configured to receive the rendered graphical image and to display the rendered graphical image comprising the first implantable medical device positioned on the surface of the skull model and the one or more image annotations superimposed onto the skull model.

10. The system of claim 9, wherein the separation distance comprises a minimum separation distance that defines a required minimum separation to be maintained between the first implantable medical device and the second implantable medical device to be implanted on the skull of the patient being modeled by the skull model.

11. The system of claim 9, wherein the separation distance comprises a maximum separation distance that defines a maximum allowable separation between the first implantable medical device and the second implantable medical device to be implanted on the skull of the patient being modeled by the skull model.

12. The system of claim 9, wherein the processing circuit is further configured to:
    receive an input selecting the graphical image comprising the first implantable medical device;
    receive an input that repositions the first implantable medical device at a new location relative to the skull model;
    re-render the boundary line superimposed onto the skull model based on the new location of the first implantable medical device; and
    output for display at the display device the re-rendered graphical image comprising the boundary line superimposed on the skull model based on the new location of the first implantable medical device.

13. The system of claim 9, wherein the processing circuit is further configured to:
    receive an input providing the separation distance defined for the first implantable medical device;
    re-render the boundary line superimposed onto the skull model based on the separation distance; and
    output for display at the display device the re-rendered graphical image comprising the boundary line superimposed on the skull model based on the separation distance.

14. The system of claim 9, wherein the processing circuit is further configured to:
    receive an input indicating a selection of a different implantable medical device to replace the first implantable medical device in the graphical image comprising the skull model;
    re-render the boundary line superimposed onto the skull model based on a different separation distance associated with the different implantable medical device; and
    output for display at the display device the re-rendered graphical image comprising the different implantable medical device positioned on the surface of the skull model and the boundary line superimposed on the skull model based on the different separation distance associated with the different implantable medical device.

15. The system of claim 9, wherein, to render the graphical image comprising the first implantable medical device positioned on the surface of the skull model, the processing circuit is further configured to:
    render a graphical image of the first implantable medical device positioned on the surface of the skull model; and
    render a graphical image of one or more leads coupled between the graphical image of the first implantable medical device and a graphical image of one or more burr holes located on the skull model;
    wherein the graphical image of the one or more leads is configured to allow selection of the one or more leads in the graphical image, and to manipulate the routing of the graphical image of the one or more leads between the graphical image of the first implantable medical device and the graphical image of the one or more burr holes.

16. A non-transitory computer readable storage medium comprising instructions for causing processing circuitry to:
    receive an image data of a head of a patient;
    receive an indication of one or more selected evaluation parameters including at least a separation distance defined between a first implantable medical device and a second implantable medical device;
    render a graphical image comprising the first implantable medical device positioned on a surface of a skull model based on the image data, the skull model comprising one or more image annotations comprising at least a boundary line superimposed onto the skull model indicative of an area of the surface of the skull model located within the separation distance relative to the position of the first implantable medical device, the image annotations determined based on an evaluation of the one or more selected evaluation parameters; and
    output the rendered graphical image comprising the first implantable medical device positioned on the surface of the skull model and the one or more image annotations superimposed onto the skull model for display at a display device.

17. The non-transitory computer readable storage medium of claim 16,
    wherein the separation distance comprises a minimum separation distance that defines a required minimum separation to be maintained between the first implantable medical device and the second implantable medical device to be implanted on the skull of the patient being modeled by the skull model.

* * * * *